United States Patent
Ayaz et al.

(10) Patent No.: US 9,946,344 B2
(45) Date of Patent: Apr. 17, 2018

(54) FUNCTIONAL NEAR INFRARED SPECTROSCOPY BASED BRAIN COMPUTER INTERFACE

(75) Inventors: Hasan Ayaz, Philadelphia, PA (US); Patricia A. Shewokis, Narberth, PA (US); Scott C. Bunce, Hummelstown, PA (US); Banu Onaral, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 515 days.

(21) Appl. No.: 14/007,203

(22) PCT Filed: Mar. 23, 2012

(86) PCT No.: PCT/US2012/030453
§ 371 (c)(1),
(2), (4) Date: Dec. 5, 2013

(87) PCT Pub. No.: WO2012/135068
PCT Pub. Date: Oct. 4, 2012

(65) Prior Publication Data
US 2015/0038812 A1 Feb. 5, 2015

Related U.S. Application Data

(60) Provisional application No. 61/467,924, filed on Mar. 25, 2011.

(51) Int. Cl.
*A61B 5/1455* (2006.01)
*G06F 3/01* (2006.01)
*A61B 5/00* (2006.01)

(52) U.S. Cl.
CPC ............ *G06F 3/015* (2013.01); *A61B 5/0075* (2013.01); *A61B 5/14553* (2013.01);
(Continued)

(58) Field of Classification Search
CPC ........ A61B 5/1455; A61B 5/72; A61B 5/7271
See application file for complete search history.

(56) References Cited

U.S. PATENT DOCUMENTS 5,724,987 A 3/1998 Gevins
5,995,857 A 11/1999 Toomim et al.
(Continued)

FOREIGN PATENT DOCUMENTS

WO    WO 2006/071891    7/2006

OTHER PUBLICATIONS

Abdelnour, A. F. and T. Huppert "Real-time imaging of human brain function by near-infrared spectroscopy using an adaptive general linear model." Neuroimage, May 2009, 46(1): 133-143.
(Continued)

*Primary Examiner* — Eric Winakur
(74) *Attorney, Agent, or Firm* — Baker & Hostetler, LLP

(57) ABSTRACT

Described herein are fNIR-based brain computer interfaces. Training of individuals to intentionally control neural activity in specific cortical areas, thereby up-regulating and down-regulating oxygenation levels in specific locations in the brain is also provided herein. Further, continuous and/or binary control over computing environments using fNIR brain computer interfaces. Further still, a scale for brain interface index for oxygenation of a portion of the brain is provided herein.

33 Claims, 11 Drawing Sheets

(52) U.S. Cl.
CPC ............ *A61B 5/486* (2013.01); *A61B 5/6814* (2013.01); *A61B 5/0042* (2013.01)

(56) References Cited

U.S. PATENT DOCUMENTS

| | | | |
|---|---|---|---|
| 6,723,047 B1 * | 4/2004 | Yamamoto | A61B 5/486 128/905 |
| 7,065,392 B2 | 6/2006 | Kato | |
| 2009/0221928 A1 | 9/2009 | Einav | |

OTHER PUBLICATIONS

Abibullaev, et al. "Functional Near Infrared Spectroscopy Based Congitive Task Classification Using Support Vector Machines, Health Informatics and Bioinformatics (HIBIT)", Apr. 20-22, 2010, 5th International Symposium on, IEEE, Antalya,Turkey.

Ang, et al. "A Brain-Computer Interface for Mental Arithmetic Task from Single-Trial Near-Infrared Spectroscopy Brain Signals"., 20th International Conference on Pattern Recognition, Istanbul, Turkey, 2010, 3764-3767.

Ayaz et al, "Assessment of Cognitive Neural Correlates for a Functional Near Infrared-Based Brain Computer Interface System", Foundations of Augmented Cognition, Neuroergonomics and Operational Neuroscience, Springer Berlin Heidelberg, 2009, 5638, 699-708.

Ayaz et al. "Using Maze Suite and Functional Near Infrared Spectroscopy to Study Learning in Spatial Navigation." Oct. 2011, Journal of Visualized Experiments, 56, | e3443, Published online: Oct. 8, 2011.

Ayaz et al. "Cognitive Workload Assessment of Air Traffic Controllers Using Optical Brain Imaging Sensors", Advances in Understanding Human Performance: Neuroergonomics, Human Factors Design, and Special Populations. T. Marek, W. Karwowski and V. Rice, CRC Press Taylor & Francis Group: 2010, 21-31.

Ayaz, H. and B. Onaral, "Analytical Software and Stimulus-Presentation Platform to Utilize, Visualize and Analyze Near-Infrared Spectroscopy Measures", 2005, Doctoral dissertation, Drexel University, Philadelphia, PA.

Ayaz, H., et al. "Registering fNIR Data to Brain Surface Image Using MRI Templates." Conf. Proc. IEEE Eng Med Bioi Soc, Aug. 30-Sep. 3, 2006, 2671-2674.

Ayaz, H., et al. "Sliding-window Motion Artifact Rejection for Functional Near-Infrared Spectroscopy." $32^{nd}$ Annual International Conference of the IEEE, Eng. Med. Bioi. Soc., Aug. 31-Sep. 4, 2010, 6567-6570.

Ayaz, H., et al. (2007). "Detecting Cognitive Activity Related Hemodynamic Signal for Brain Computer Interface Using Functional Near Infrared Spectroscopy." Proceedings of the 3rd IEEE/EMBS Conference on Neural Engineering, Kohala coast, Hawaii, May 2-5, 2007, 342-345.

Ayaz, H., S. L. Allen, et al. "Maze Suite 1.0: A Complete Set of Tools to Prepare, Present, and Analyze Navigational and Spatial Cognitive Neuroscience Experiments." 2008, Behav. Res. Methods, 40(1):353-359.

Bartocci et al. "Activation of Olfactory Cortex in Newborn Infants After Odor Stimulation: A Functional Near-Infrared Spectroscopy Study." 2000, Pediatr. Res. 48(1), 18-23.

Bauernfeind et al. "Development, set-up and first results for a one-channel near-infrared spectroscopy system." Feb. 2008, Biomed. Tech. (Berl), 53(1), 36-43.

Becerra, et al. "Follow-up Study of Learning-Disabled Children Treated With Neurofeedback or Placebo." Jul. 2006, Clinical EEG and Neuroscience, 37(3),198.

Bentley et al. "An offline Auditory P300 Brain-Computer Interface Using Principal and Independent Component Analysis Techniques for Functional Electrical Stimulation Application." Conf Proc IEEE, Eng. Med. Bioi. Soc., Aug. 20-25, 2008: 4660-4663.

Berger, H. "Uber das elektrenkephalogramm des menschen." European Archives of Psychiatry and Clinical Neuroscience, Apr. 1929, 87(1): 527-570. Abstract attached.

Birbaumer et al. "A Spelling Device for the Paralysed," Mar. 25, 1999, Nature, 398(6725): 297-298.

Birbaumer, N. "Brain-Computer-Interface Research: Coming of age." Clinical Neurophysiology, Mar. 2006, 117(3), 479-483.

Birbaumer, N. "Breaking the Silence: Brain-Computer Interfaces (BCI) for Communication and Motor Control." Psychophysiology, Nov. 2006, 43(6): 517-532.

Birbaumer, N. and L. G. Cohen "Brain-Computer Interfaces: Communication and Restoration of Movement in Paralysis." Mar. 2007, The Journal of Physiology, 579(3), 621-636.

Birbaumer, "Slow Cortical Potentials: Plasticity, Operant Control, and Behavioral Effects." , The Neuroscientist, Mar. 1999, 5(2), 74-78.

Birbaumer et al. "Brain-Computer Interface in Paralysis." Current Opinion in Neurology, Dec. 2008, 21(6): 634-638.

Blankertz, et al. "The Non-Invasive Berlin Brain-Computer Interface: Fast Acquisition of Effective Performance in Untrained Subjects." 2007, Neuroimage, 37(2): 539-550.

Boas et al. "The Accuracy of Near Infrared Spectroscopy and Imaging during Focal Changes in Cerebral Hemodynamics." 2001, Neuroimage, 13(1): 76-90.

Boly, et al. "When Thoughts Become Action: An fMRI Paradigm to Study Volitional Brain Activity in Non-Communicative Brain Injured Patients." Neuroimage, Jul. 1, 2007, 36(3), 979-992.

Bozkurt et al. "A Portable Near Infrared Spectroscopy System for Bedside Monitoring of Newborn Brain." Apr. 29, 2005, Biomed. Eng. Online, 4(1), 29.

Brunner et al. "Does the'P300' Speller Depend on Eye Gaze?" Oct. 2010, J. Neural. Eng., 7(5):056013, Epublished on Sep. 21, 2010.

Bunce, et al. "Functional Near-Infrared Spectroscopy: An Emerging Neuroimaging Modality." IEEE Eng. Med. Bioi. Mag., Jul. and Aug. 2006, 25(4), 54-62.

Caria et al. "Regulation of Anterior Insular Cortex Activity Using Real-Time fMRI." , Neuroimage, Jan. 2007, 35(3), 1238-1246.

Cerf et al. "On-line, Voluntary Control of Human Temporal Lobe Neurons.", Nature, Oct. 2010, 467(7319), 1104-1108.

Chance et al. "Cognition-Activated Low-Frequency Modulation of Light Absorption in Human Brain." Jan. 1993, Proc. Natl. Acad. Sci. USA, 90(8), 3770-3774.

Chance, B. "Near-Infrared Images Using Continuous, Phase-Modulated, and Pulsed Light With Quantitation of Blood and Blood Oxygenation." 1998, Ann. NY Acad. Sci., 838(1), 29-45.

Chance, et al. "A novel method for fast imaging of brain function, non-invasively, with light." Optics Express, Feb. 1998, 2(10): 411-423.

Chance, B., Q. Luo, et al. "Optical Investigations of Physiology: A Study of Intrinsic and Extrinsic Biomedical Contrast." Philos. Trans. R. Soc. Land. B. Bioi. Sci ., 1997, 352(1354), 707-716.

Chatrian et al. "Depth Electrographic Study of a Fast Rhythm Evoked From the Human Calcarine Region by Steady Illumination." Electroencephalogr. Clin. Neurophysiol., Feb. 1960, 12(1), 167-176.

Chau, T. and S. Damouras "Reply to On the Risk of Extracting Relevant Information From Random Data", J. Neural. Eng., 2009, 6(5), 058002.

Coben et al. "Neurofeedback for Autistic Spectrum Disorder: A Review of the Literature.", Applied Psychophysiology and Biofeedback, Mar. 2010, 35(1), 83-105.

Cope, M. "The Development of a Near Infrared Spectroscopy System and Its Application for Non Invasive Monitoring of Cerebral Blood and Tissue Oxygenation in the Newborn Infant", 1991, Doctoral dissertation, London, University College London.

Coyle et al. "Brain-Computer Interface Using a Simplified Functional Near-Infrared Spectroscopy System." 2007, J. Neural. Eng., 4(3), 219-226.

Coyle et al. "On the Suitability of Near-Infrared (NIR) Systems for Next-Generation Brain-Computer Interfaces." , Physiol. Meas., Aug. 2004, 25(4), 815-822.

(56) References Cited

OTHER PUBLICATIONS

Csibra et al. "Near Infrared Spectroscopy Reveals Neural Activation During Face Perception in Infants and Adults." Apr.-Jun. 2004, Journal of Pediatric Neurology 2(2), 85-89.

Cui, et al. "Functional Near Infrared Spectroscopy (NIRS) Signal Improvement Based on Negative Correlation Between Oxygenated and Deoxygenated Hemoglobin Dynamics.", Neuroimage, Nov. 2009, 49(4), 3039-3046.

Curio, et al. "Localization of Evoked Neuromagnetic 600 Hz Activity in the Cerebral Somatosensory System.", Electroencephalogr. Clin. Neurophysiol., Dec. 1994, 91(6), 483-487.

Curran, E. "Learning to Control Brain Activity: A Review of the Production and Control of Eeg Components for Driving Brain-Computer Interface (BCI) Systems." Brain and Cognition, Apr. 2003, 51(3), 326-336.

Daly, J. and J. Wolpaw, "Brain-Computer Interfaces in Neurological Rehabilitation.", The Lancet Neurology, 2008, 7(11), 1032-1043, Published online: Oct. 3, 2008.

DeCharms et al. "Control Over Brain Activation and Pain Learned by Using Real-Time Functional MRI.", Proc. Natl. Acad. Sci. USA, Dec. 20, 2005, 102(51), 18626-18631.

DeCharms et al. "Learned Regulation of Spatially Localized Brain Activation Using Real-Time fMRI.", Neuroimage, 2004, 21(1), 436-443.

Decharms, R. C. "Reading and Controlling Human Brain Activation Using Real-Time Functional Magnetic Resonance Imaging.", Trends Cogn. Sci., Nov. 2007, 11(11), 473-481.

Delpy et al. "Estimation of Optical Pathlength Through Tissue From Direct Time of Flight Measurement.", Physics in Medicine and Biology, Dec. 1988, 33(12), 1433.

Duschek et al. "Self-Regulation of Cerebral Blood Flow by Means of Transcranial Doppler Sonography Biofeedback." Annals of Behavioral Medicine, Apr. 2011, 41(2), 235-242.

Eippert et al. "Regulation of Emotional Responses Elicited by Threat-Related Stimuli.", , Hum. Brain Mapp., May 2007, 28(5), 409-423.

Elwell, C., M. Cope, et al. "Quantification of Adult Cerebral Hemodynamics by Near-Infrared Spectroscopy." Journal of Applied Physiology, 1994, 77(6), 2753.

Epstein, L. and E. Blanchard, "Biofeedback, Self-control, and Self-management." , Applied Psychophysiology and Biofeedback, 1977, 2(2), 201-211.

Farwell, L. and E. Donchin, "Talking Off the Top of Your Head: Toward a Mental Prosthesis Utilizing Event-Related Brain Potentials." Electroencephalogr, 1988, Clin. Neurophysiol, Dec. 1988, 70(6), 510-523.

Farwell, L. and E. Donchin, "The truth will out: Interrogative Polygraphy ("lie detection") With Event-Related Brain Potentials." Sep. 1991, Psychophysiology, 28(5), 531-547.

Fellows, L. "Deciding How to Decide: Ventromedial Frontal Lobe Damage Affects Information Acquisition in Multi-Attribute Decision Making." Brain, Feb. 2, 2006, 129(4), 944.

Fetz, E. E. "Volitional Control of Neural Activity: Implications for Brain-Computer Interfaces.", Physioi, Mar. 15, 2007, 579(Pt 3), 571-579.

Fuster, J. "The Prefrontal Cortex—An Update: Time is of the Essence.", Neuron, May 2001, 30(2), 319-334.

Gevensleben et al, "Is Neurofeedback an Efficacious Treatment for ADHD? A Randomised Controlled Clinical Trial.", Journal of Child Psychology and Psychiatry, Jul. 2009, 50(7), 780-789.

Greenwood, P. M. and R. Parasuraman, "Neuronal and Cognitive Plasticity: A Neurocognitive Framework for Ameliorating Cognitive Aging.", Frontiers in Aging Neuroscience, Nov. 2010, 2,12.

Guger et al. "How Many People are Able to Control a P300-Based Brain-Computer Interface (BCI)?" Sep. 18, 2009, Neurosci. Lett. In Press, 462(1), 94-98.

Haida et al, "Brain Function of an ALS Patient in Complete Locked-In State by using Optical Topography", The Frontier of Mind-Brain Science and Its Practical Applications. H. Koizumi. Tokyo, Japan, Hitachi. 2000, 2, 95-97.

Hatsopoulos, N. G. and J. P. Donoghue, "The Science of Neural Interface Systems." Jul. 2009, Annual Review of Neuroscience, 32(1), 249-266.

Heeger, D. J. and D. Ress, "What Does fMRI Tell Us About Neuronal Activity?" Nat. Rev. Neurosci., Feb. 2002, 3(2),142-151.

Herrmann, C. and T. Demiralp, "Human EEG Gamma Oscillations in Neuropsychiatric Disorders." Clin. Neurophysiol, Dec. 2005, 116(12), 2719-2733.

Hinterberger et al. "An EEG-Driven Brain-Computer Interface Combined With Functional Magnetic Resonance Imaging (fMRI)." IEEE Trans. Biomed. Eng., Jun. 2004, 51(6), 971-974.

Hinterberger et al. "Brain Areas Activated in fMRI During Self-Regulation of Slow Cortical Potentials (SCPs)." Exp Brain Res., 2003,152(1), 113-122, Published Online: Jun. 27, 2003.

Hintze, J., "NCSS, PASS, and GESS", 2007, Kaysville. Utah, www.ncss.com.

Hochberg, L. and J. Donoghue, "Sensors for Brain-Computer Interfaces." Engineering in Medicine and Biology Magazine, Oct. 2006, IEEE, 25(5), 32-38.

Hoffman et al. "EEG Neurofeedback in the Treatment of Mild Traumatic Brain Injury." Abstract presented at Meeting of the American Medical EEG Association Feb. 23-24, 1996, Clinical Electroencephalography, 1996, 27(2), p. 4 of 5.

Holper, L. and Wolf, M., "Motor Imagery in Response to Fake Feedback Measured by Functional Near-Infrared Spectroscopy", NeuroImage, Mar. 2010, 50, 190-197.

Hoshi et al. "Non-Synchronous Behavior of Neuronal Activity, Oxidative Metabolism and Blood Supply During Mental Tasks in Man." Neurosci. Lett., May 1994, 172(1-2), 129-133.

Hoshi, Y. and M. Tamura, "Detection of Dynamic Changes in Cerebral Oxygenation Coupled to Neuronal Function During Mental Work in Man." Neurosci. Lett., Feb. 5, 1993, 150(1), 5.

Hoshi, Y. and M. Tamura, "Near-Infrared Optical Detection of Sequential Brain Activation in the Prefrontal Cortex During Mental Tasks." Neuroimage, 1997, 5(4 Pt 1), 292-297.

Huppert et al. "HomER: A Review of Time-Series Analysis Methods for Near-Infrared Spectroscopy of the Brain." Appl. Opt., Apr. 1, 2009, 48(10), D280-D298.

International Patent Application No. PCT/US2012/30453: International Search Report and Written Opinion dated Sep. 10, 2012, 15 Pages.

Izzetoglu et al, "Motion Artifact Cancellation in NIR Spectroscopy Using Discrete Kalman Filtering." 2010, Biomed. Eng. Online, 9(1),16.

Izzetoglu et al. "Motion Artifact Cancellation in NIR Spectroscopy Using Wiener Filtering." IEEE, Trans. Biomed. Eng., 2005, 52(5), 934-938.

Jarusiewicz, "Efficacy of Neurofeedback for Children in the Autistic Spectrum: A Pilot Study." Journal of Neurotherapy, 2002, 6(4), 39-49, Published Online: Sep. 8, 2008.

Jobsis, F. F. "Noninvasive, Infrared Monitoring of Cerebral and Myocardial Oxygen Sufficiency and Circulatory Parameters." Science, Dec. 23, 1977, 198(4323),1264-1267.

Johnston et al. "Neurofeedback: A Promising Tool for the Self-Regulation of Emotion Networks." Neuroimage, Jan. 1, 2010, 49(1), 1066-1072.

Kato, T., A. Kamei, et al. "Human Visual Cortical Function During Photic Stimulation Monitoring by Means of Near-Infrared Spectroscopy." Journal of Cerebral Blood Flow and Metabolism, 1993, 13(3), 516-520.

Kelly et al. "Visual Spatial Attention Tracking Using High-Density SSVEP Data for Independent Brain-Computer Communication." Neural Systems and Rehabilitation Engineering, IEEE Transactions on 2005, 13(2), 172-178.

Kouijzer et al, "Neurofeedback Improves Executive Functioning in Children With Autism Spectrum Disorders." Research in Autism Spectrum Disorders, Jan. 2009, 3(1), 145-162.

Krauss, G. and R. Fisher, The Johns Hopkins Atlas of Digital EEG: An Interactive Training Guide, 2006, Johns Hopkins University Press.

(56) References Cited

OTHER PUBLICATIONS

Krepki et al, "The Berlin Brain-Computer Interface (BBCI)—Towards a New Communication Channel for Online Control in Gaming Applications." Multimedia Tools Appl., Apr. 2007, 33(1), 73-90.

Krusienski et al. "Toward Enhanced P300 Speller Performance." J. Neurosci. Methods, Jan. 15, 2008, 167(1), 15-21.

Kübler et al. "Brain-Computer Communication: Self-Regulation of Slow Cortical Potentials for Verbal Communication." Arch. Phys. Med. Rehabil., Nov. 2001, 82(11), 1533-1539.

Kübler et al. "Patients With ALS Can Use Sensorimotor Rhythms to Operate a Brain-Computer Interface." Neurology, 2005, 64(10), 1775-1777.

Kubler, et al. "A Brain-Computer Interface Controlled Auditory Event-Related Potential (p300) Spelling System for Locked-In Patients." Ann. NY Acad. Sci., Mar. 2009, 1157, 90-100.

LaConte et al, "Real-Time fMRI Using Brain-State Classification." Hum. Brain Mapp., Oct. 2007, 28(10),1033-1044.

LaConte, S., "Decoding fMRI Brain States in Real-Time." Neuroimage, 2010, 56, 440-454.

Lebedev, M. and M. Nicolelis, "Brain-Machine Interfaces: Past, Present and Future." Trends Neurosci., Sep. 2006, 29(9), 536-546.

Lee, et al. "Brain-Machine Interface via Real-Time fMRI: Preliminary Study on Thought-Controlled Robotic Arm." Neurosci Lett., 2009, 450(1), 1-6.

Leins et al, "Neurofeedback for children with ADHD: A Comparison of SCP and theta/beta protocols." Applied Psychophysiology and Biofeedback, 2007, 32(2), 73-88, Publsihed Online: Mar. 14, 2007.

Leuthardt et al, "Evolution of Brain-Computer Interfaces: Going Beyond Classic Motor Physiology." Neurosurg. Focus, Jul. 2009, 27(1), E4.

Levine et al, "A Direct Brain Interface Based on Event-Related Potentials." Rehabilitation Engineering, Jun. 2002, IEEE Transactions on 8(2), 180-185.

Limongi et al, "Detecting Mental Calculation Related Frontal Cortex Oxygenation Changes for Brain Computer Interface Using Multi-Channel Functional Near Infrared. Topography." International Journal of Bioelectromagnetism, 2009, 11(2), 86-90.

Logothetis et al, "Neurophysiological Investigation of the Basis of the fMRI Signal." Nature, Jul. 12, 2001, 412(6843), 150-157.

Logothetis, N. K. , "The Neural Basis of the Blood-Oxygen-Level-Dependent Functional Magnetic Resonance Imaging Signal." Philos. Trans. R Soc. Lond. B Bioi. Sci., Aug. 2, 2002, 357(1424), 1003-1037.

Logothetis, N. K. and B. A. Wendell, "Interpreting the BOLD Signal." Annu. Rev. Physiol., Mar. 2004, 66, 735-769.

Lubar et al, "Evaluation of the Effectiveness of EEG Neurofeedback Training for Adhd in a Clinical Setting as Measured by Changes in TOVA Scores, Behavioral Ratings, and WISC-R Performance." Applied Psychophysiology and Biofeedback, 1995, 20(1), 83-99.

Lubar, J. F. and W. W. Bahler, "Behavioral Management of Epileptic Seizures Following Eeg Biofeedback Training of the Sensorimotor Rhythm." Biofeedback Self Regul, Mar. 1976, 1(1), 77-104.

Lubar, J. and J. Lubar, "Electroencephalographic Biofeedback of SMR and Beta for Treatment of Attention Deficit Disorders in a Clinical Setting." Applied Psychophysiology and Biofeedback, 1984, 9(1),1-23.

Luu, S. and T. Chau, "Decoding Subjective Preference From Single-Trial Near-Infrared Spectroscopy Signals." J. Neural. Eng., 2009, 6(1), 16003.

Izzetoglu et al, "Functional Optical Brain Imaging Using Near-Infrared During Cognitive Tasks." International Journal of Human-Computer Interaction, 2004, 17(2), 211-227, Published Online: Jun. 9, 2010.

Izzetoglu et al. "Functional Near-Infrared Neuroimaging." IEEE, Trans. Neural. Syst. Rehabil. Eng., Jun. 2005,13(2),153-159.

Izzetoglu, K. and B. Onaral, "Neural Correlates of Cognitive Workload and Anesthetic Depth: fNIR Spectroscopy Investigation in Humans", Philadelphia, PA, Drexel University: 2008, xv, 72 leaves.

Malonek, D. and A. Grinvald, "Interactions Between Electrical Activity and Cortical Microcirculation Revealed by Imaging Spectroscopy: Implications for Functional Brain Mapping." Science, 1996, 272(5261), 551-554.

Manes et al, "Decision-Making Processes Following Damage to the Prefrontal Cortex." Brain, Mar. 2002, 125(3), 624-639.

Mappus IV et al, "An fNIR Based BMI for Letter Construction Using Continuous Control", CHI 2009, Apr. 4-9, 2009, Boston, MA, USA, 1-6 pages.

Matsuyama, H., H. Asama, et al, "Design of differential Near-Infrared Spectroscopy based Brain Machine Interface". The 18th IEEE International Symposium on Robot and Human Interactive Communication. Toyama, Japan., 2009.

Matthews et al. "Hemodynamics for Brain-Computer Interfaces." Signal Processing Magazine, Jan. 2008, IEEE, 25(1), 87-94.

Maxwell, S. and H. Delaney, "Designing Experiments and Analyzing Data: A Model Comparison Perspective", NY, Psychology Pres., 2004.

Mayhew, J. E. "A Measured Look at Neuronal Oxygen Consumption." Science, 2003, 299(5609): 1023-1024.

Meek, J. H., M. Firbank, et al. "Regional Hemodynamic Responses to Visual Stimulation in Awake Infants." Pediatric Research, 1998, 43(6), 840.

Meek, J., C. Elwell, et al, "Regional Changes in Cerebral Haemodynamics as a Result of a Visual Stimulus Measured by Near Infrared Spectroscopy." Proceedings: Biological Sciences, 1995, 261(1362), 351-356.

Middendorf, M., G. McMillan, et al, "Brain-Computer Interfaces Based on the Steady-State Visual-Evoked Response." Rehabilitation Engineering, Jun. 2000, IEEE Transactions on 8(2), 211-214.

Millan et al, "Combining Brain-Computer Interfaces and Assistive Technologies: State-of-the-Art and Challenges." Frontiers in Neuroscience, Sep. 7, 2010, 4(161), 1-15.

Monastra, V. "Clinical Applications of Electroencephalographic Biofeedback." Biofeedback: A practitioners guide: 2003, 438-463.

Monastra, V. "Electroencephalographic Biofeedback (neurotherapy) as a Treatment for Attention Deficit Hyperactivity Disorder: Rationale and Empirical Foundation." Child and Adolescent Psychiatric Clinics of North America, 2005, 14(1), 55-82.

Moore, N. "A Review of EEG Biofeedback Treatment of Anxiety Disorders." Clinical EEG (electroencephalography), 2000, 31(1), 1.

Moran, D. "Evolution of Brain-Computer Interface: Action Potentials, Local Field Potentials and Electrocorticograms." Current Opinion in Neurobiology, Dec. 2010, 20(6), 741-745.

Muller-Putz, G. and G. Pfurtscheller, "Control of an Electrical Prosthesis With an SSVEP-Based BCI." Biomedical Engineering, 2007, IEEE Transactions on 55(1): 361-364.

Naito, M., Y. Michioka, et al. "A Communication Means for Totally Locked-in ALS Patients Based on Changes in Cerebral Blood Volume Measured with Near-Infrared Light." IEICE Trans Inf Syst., 2007, E90-D(7),1028-1037.

Nicolelis, M. A. L. and M. A. Lebedev, "Principles of Neural Ensemble Physiology Underlying the Operation of Brain-Machine Interfaces." Nature Reviews Neuroscience, Jul. 2009, 10(7), 530-540.

Niedermeyer, E. "The Normal EEG of the Waking Adult. Electroencephalography: Basic Principles. Clinical Applications, and Related Fields", E. Niedermeyer and F. Lopes da Silva. Baltimore, Williams & Wilkins: 2005, 167-180.

Nijboer et al. "A P300-Based Brain-Computer Interface for People With Amyotrophic Lateral Sclerosis." Clin. Neurophysioll., Aug. 2008, 19(8), 1909-1916.

Nishimura et al, "Physiologic System Interfaces Using fNIR with Tactile Feedback for Improving Operator Effectiveness", Augmented Cognition, HCII, 2007, LNAI 4565, pp. 323-328.

Obrig et al, "Near-Infrared Spectroscopy: Does It Function in Functional Activation Studies of the Adult Brain?" International Journal of Psychophysiology, Mar. 1, 2000, 35(2-3), 125-142.

(56) References Cited

OTHER PUBLICATIONS

Obrig et al, , "Cerebral Oxygenation Changes in Response to Motor Stimulation." LAP . . . PI Physiol., 1996, 81(3),1174-1183.
Ogata et al, "A Study on the Frontal Cortex in Cognitive Tasks using Near-Infrared Spectroscopy", Engineering in Medicine and Biology Society, 2007. EMBS 2007. 29th Annual International Conference of the IEEE, 2007.
Ogawa et al, "Brain Magnetic Resonance Imaging With Contrast Dependent on Blood Oxygenation." Proc. Natl. Acad. Sci., USA, Dec. 1990, 87(24), 9868-9872.
Okamoto et al. "Multimodal Assessment of Cortical Activation During Apple Peeling by NIRS and fMRI." Neuroimage, 2004, 21(4), 1275-1288.
Oldfield, R. C., "The Assessment and Analysis of Handedness: The Edinburgh Inventory." Neuropsychologia, 1971, 9(1), 97-113.
Orlando, P. and R. Rivera, "Neurofeedback for Elementary Students With Identified Learning Problems." Journal of Neurotherapy, 2004, 8(2), 5-19.
Othmer, S. and S. Othmer, "Post Traumatic Stress Disorder—The Neurofeedback Remedy." Biofeedback, 2009, 37(1), 24-31.
Oum, K., H. Ayaz, et al. "MindTactics: A Brain Computer Interface Gaming Platform", $2^{nd}$ International IEEE Games Innovation Conference Hong Kong, China, IEEE., Dec. 21-23, 2010.
Pfurtscheller, G. and F. Lopes da Silva, "Event-related EEG/MEG Synchronization and Desynchronization: Basic Principles." Clinical Neurophysiology, 1999, 110(11),1842-1857.
Pfurtscheller, G. and C. Neuper, "Motor Imagery and Direct Brain-Computer Communication." 2002, Proceedings of the IEEE, 89(7), 1123-1134.
Pfurtscheller, G., G. R. Muller-Putz, et al. "Rehabilitation with Brain-Computer Interface Systems." Computer, Oct. 2008, 41(10), 58-65.
Pfurtscheller, G., R. Leeb, et al. "Walking from thought." Brain Res., 2006, 1071(1), 145-152.
Pham et al, "An Auditory Brain-Computer Interface Based on the Self-Regulation of Slow Cortical Potentials." Neurorehabil Neural Repair, 2005, 19(3), 206-218.
Posse et al. "Real-time fMRI of Temporolimbic Regions Detects Amygdala Activation During Single-Trial Self-Induced Sadness." Neuroimage, 2003, 18(3), 760-768.
Power et al. "Classification of Prefrontal Activity Due to Mental Arithmetic and Music Imagery." J. Neural. Eng., Feb. 2010, 7,1-10.
Rapoport et al, "Engaging, Non-Invasive Brain-Computer Interfaces (BCIs) for Improving Training Effectiveness & Enabling Creative Expression", Proceedings of the Human Factors and Ergonomics Society Annual Meeting, 2008, 52(7), SAGE Publications.
Rosenfeld et al, "Simple, Effective Countermeasures to P300 Based Tests of Detection of Concealed Information." Psychophysiology, 2004, 41(2): 205-219.
Rostrup et al, "The Relationship Between Cerebral Blood Flow and Volume in Humans." Neuroimage, 2005, 24(1),1-11.
Rota et al, "Reorganization of Functional and Effective Connectivity During Real-Time Fmri-Bci Modulation of Prosody Processing." Brain and Language in Press, Jun. 2011, 117(3), 123-132.
Rota et al. "Self-Regulation of Regional Cortical Activity Using Real-Time fMRI: The Right Inferior Frontal Gyrus and Linguistic Processing." Hum. Brain Mapp., 2009, 30(5), 1605-1614.
Sagara et al. "Portable Single-Channel NIRS-Based BMI System for Motor Disabilities' Communication Tools", Engineering in Medicine and Biology Society, Sep. 2009, 31st Annual International Conference of the IEEE EMBS, Minneapolis, Minnesota, USA, 602-605.
Sakatani et al, "Cerebral Blood Oxygenation Changes Induced by Auditory Stimulation in Newborn Infants Measured by Near Infrared Spectroscopy." Jul. 1999, Early Human Development, 55(3), 229-236.
Sakatani et al. "Comparison of Blood-Oxygen-Level-Dependent Functional Magnetic Resonance Imaging and Near-Infrared Spectroscopy Recording During Functional Brain Activation in Patients With Stroke and Brain Tumors." Journal of Biomedical Optics, 2007, 12(6), 062110.
Sambasivan, Designing Pervasive Brain-Computer Interfaces. HCI and Usability for Medicine and Health Care, Third Symposium of the Workgroup Human-Computer Interaction and Usability Engineering of the Austrian Computer Society, USAB 2007. A. Holzinger. Graz, Austria, Proceedings. Springer. LNCS, 2007, 4799: 267-272.
Sato et al, "Temporal Cortex Activation During Speech Recognition: An Optical Topography Study." 1999, Cognition, 73(3), B55-66.
Seifert, A. and J. Lubar, "Reduction of Epileptic Seizures Through Eeg Biofeedback Training." Biological Psychology, 1975, 3(3), 157-184.
Simons et al. "Distinct Roles for Lateral and Medial Anterior Prefrontal Cortex in Contextual Recollection." Journal of Neurophysiology, Jul. 2005, 94(1), 813.
Sitaram et al. "Hemodynamic Brain-Computer Interfaces for Communication and Rehabilitation." Neural Netw., 2009, 22(9), 1320-1328.
Sitaram et al, "Temporal Classification of Multichannel Near-Infrared Spectroscopy Signals of Motor Imagery for Developing a Brain-Computer Interface." NeuroImage, 2007, 34(4), 1416-1427.
Sitaram et al. "FMRI Brain-Computer Interface: A Tool for Neuroscientific Research and Treatment." Comput. Intell. Neurosci., 2007, 25487, 10 pages.
Sitaram et al. "fMRI Brain-Computer Interfaces." Signal Processing Magazine, IEEE, 2007, 25(1), 95-106, Jan. 2008.
Ranganatha et al. "Near Infrared Spectroscopy Based Brain-Computer Interface", Proc. SPIE Exp. Mech., Bellingham,WA, SPIE., Third International Conference, 2005, 5852, 434-442.
Smith, W. "The Effect of Neurofeedback Training on PTSD Symptoms of Depression and Attention Problems Among Military Veterans.", Jun. 2008.
Soraghan et al. "A 12-Channel, Real-Time Near-Infrared Spectroscopy Instrument for Brain-Computer Interface Applications." Conf. Proc. IEEE Eng. Med. Bioi. Soc., Aug. 2008, 1, 5648-5651.
Sorger et al. "Another Kind of 'BOLD Response': Answering Multiple-Choice Questions via Online Decoded Single-Trial Brain Signals." Progress in Brain Research, 2009, 177, 275.
Sterman, M. "Physiological Origins and Functional Correlates of EEG Rhythmic Activities: Implications for Self-Regulation." Applied Psychophysiology and Biofeedback, Mar. 1996, 21(1), 3-33.
Strangman et al, "Non-invasive neuroimaging using near-infrared light." Bioi. Psychiatry, Oct. 1, 2002, 52(7), 679-693.
Thatcher, R. "QEEG and Traumatic Brain Injury: Present and Future." Brain Injury Source, 1991, 20-23.
Thompson, "Neurofeedback Combined With Training in Metacognitive Strategies: Effectiveness in Students With ADD." Appl. Psychophysiol Biofeedback, 1998, 23(4), 243-263.
Thompson, J. K. "Single-Neuron Activity and Tissue Oxygenation in the Cerebral Cortex." Science, Feb. 14, 2003, 299(5609), 1070-1072.
Toomim et al, "Intentional increase of cerebral blood oxygenation using hemoencephalography (HEG): An efficient brain exercise therapy." Journal of Neurotherapy, 2005, 8(3), 5-21.
Tsubone, et al, "Application to Robot Control Using Brain Function Measurement by Near-Infrared Spectroscopy". Engineering in Medicine and Biology Society, 2007. EMBS 2007. 29th Annual International Conference of the IEEE, Aug. 2007, 5342-5345.
Utsugi, et al. "Development of an Optical Brain-machine Interface", Engineering in Medicine and Biology Society, 2007. EMBS 2007. 29th Annual International Conference of the IEEE, 2007, 5338-5341.
Vernon et al. "Neurofeedback as a Treatment for ADHD: A Methodological Review With Implications for Future Research." Journal of Neurotherapy, 2004, 8(2), 53-82.
Vidal, J. "Toward Direct Brain-Computer Communication." Annual Review of Biophysics and Bioengineering, 1973, 2(1), 157-180.

(56) References Cited

OTHER PUBLICATIONS

Villringer et al. "Near Infrared Spectroscopy (NIRS): A New Tool to Study Hemodynamic Changes During Activation of Brain Function in Human Adults." Neurosci. Lett. 1993,154(1-2), 101-104.
Villringer, "Non-Invasive Optical Spectroscopy and Imaging of Human Brain Function." Trends Neurosci., 1997, 20(10), 435-442.
Walton et al, "Interactions Between Decision Making and Performance Monitoring Within Prefrontal Cortex." Nature Neuroscience, Nov. 2004, 7(11), 1259-1265.
Weiskopf et al. "Physiological Self-Regulation of Regional Brain Activity Using Real-Time Functional Magnetic Resonance Imaging (fMRI): Methodology and Exemplary Data." Neuroimage, Jul. 2003, 19(3), 577-586.
Weiskopf et al, "Principles of a Brain-Computer Interface (BCI) Based on Real-Time Functional Magnetic Resonance Imaging", (fMRI). IEEE Trans. Biomed. Eng., Jun. 2004, 51(6), 966-970.
Weiskopf et al, "Real-Time Functional Magnetic Resonance Imaging: Methods and Applications." Magn. Reson. Imaging., Jul. 2007, 25(6), 989-1003.
Weiskopf et al. "Self-Regulation of Local Brain Activity Using Real-Time Functional Magnetic Resonance Imaging (fMRI)." J. Physio. I Paris, Jul.-Nov. 2004, 98(4-6), 357-373.
Wing, K. ,"Effect of Neurofeedback on Motor Recovery of a Patient With Brain Injury: A Case Study and Its Implications for Stroke Rehabilitation." Topics in Stroke Rehabilitation, Fall 2001, 8(3), 45-53.
Wolpaw et al, "Brain-Computer Interfaces for Communication and Control." Clinical Neurophysiology, 2002, 113(6), 767-791.
Wolpaw, J. R. and N. Birbaumer, Brain-Computer Interfaces for Communication and Control.,. Clinical Neurophysiology, 2002, 113, 767-791.
Wolpaw, J. "Brain-Computer Interfaces as New Brain Output Pathways." The Journal of Physiology, Mar. 2007, 579(3), 613.
Wolpaw, J. R. and D. J. McFarland, "Multichannel EEG-Based Brain-Computer Communication." Electroencephalogr, Clin., Neurophysiol, Jun. 1994, 90(6), 444-449.
Wood, J. and J. Grafman, "Human Prefrontal Cortex: Processing and Representational Perspectives." Nature Reviews Neuroscience, 2003, 4(2),139-147.
Wray et al. "Characterization of the Near Infrared Absorption Spectra of Cytochrome aa3 and Haemoglobin for the Non-Invasive Monitoring of Cerebral Oxygenation." Biochimica et Biophysica Acta (BBA)—Bioenergetics, Mar. 30, 1988, 933(1),184-192.
Wriessnegger et al. "Spatia-Temporal Differences in Brain Oxygenation Between Movement Execution and Imagery: A Multichannel Near-Infrared Spectroscopy Study." Lnt. J. Psychophysiol., 2008, 67(1), 54-63.
Wubbels et al, "Exploring Calibration Techniques for Functional Near-Infrared Imaging (fNIR) Controlled Brain-Computer Interfaces." Foundations of Augmented Cognition: 2007, 23-29.
Wyatt et al. "Quantification of Cerebral Oxygenation and Haemodynamics in Sick Newborn Infants by Near Infrared Spectrophotometry." The Lancet, 1986, 328(8515), 1063-1066.
Yoo et al, "Brain-Computer Interface Using fMRI: Spatial Navigation by Thoughts." Neuroreport, Jul. 19, 2004, 15(10),1591-1595.
Yoo et al, "Neurofeedback fMRI Mediated Learning and Consolidation of Regional Brain Activation During Motor Imagery." International Journal of Imaging Systems and Technology, Jun. 2008, 18(1), 69-78.
Yoo, S. and F. Jolesz, "Functional MRI for Neurofeedback: Feasibility Study on a Hand Motor Task." Neuroreport, Aug. 2002, 13(11), 1377.
Zaramella et al, "Brain Auditory Activation Measured by Near-Infrared Spectroscopy (NIRS) in Neonates." Pediatric Research, 2001, 49(2), 213.

* cited by examiner

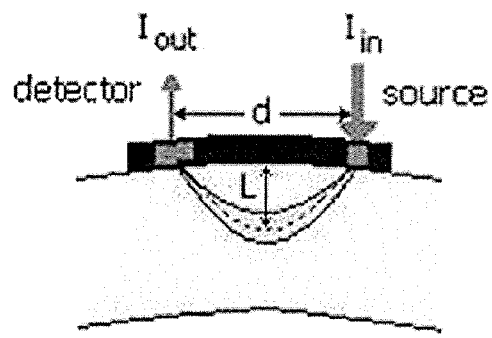

Fig. 1(a)

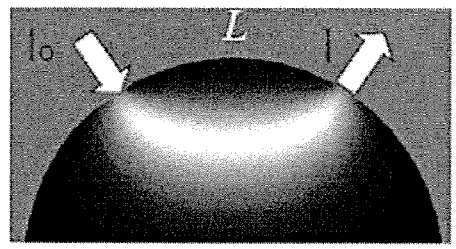

Fig. 1(b)

$$\Delta OD_\lambda = \log(\frac{I_{rest}}{I_{test}}) = \varepsilon_\lambda^{HB} . \Delta c^{HB} . d . DPF + \varepsilon_\lambda^{HBO_2} . \Delta c^{HBO_2} . d . DPF$$

↓ Measuring at two different wavelengths $$\begin{bmatrix} \Delta OD_{\lambda 1} \\ \Delta OD_{\lambda 2} \end{bmatrix} = \underbrace{\begin{bmatrix} \varepsilon_{\lambda 1}^{HB} . d . DPF & \varepsilon_{\lambda 1}^{HBO_2} . d . DPF \\ \varepsilon_{\lambda 2}^{HB} . d . DPF & \varepsilon_{\lambda 2}^{HBO_2} . d . DPF \end{bmatrix}}_{F} \begin{bmatrix} \Delta c^{HB} \\ \Delta c^{HBO_2} \end{bmatrix}$$

Fig. 1(c)

FUNCTIONAL NEAR INFRARED SPECTROSCOPY BASED BRAIN COMPUTER INTERFACE

CROSS-REFERENCE TO RELATED APPLICATIONS

This application is the National Stage of International Application No. PCT/US2012/030453, filed Mar. 23, 2012, which claims the benefit of U.S. Provisional Application No. 61/467,924, filed Mar. 25, 2011, the disclosures of which are incorporated herein by reference in their entireties for any and all purposes.

BACKGROUND

The brain is an incredibly complex organ with many signals and chemical interactions taking place at any given time. Most commonly, the brain is involved in the control of the functions of the associated body. As such, the brain can be considered to interface with the body and actions associated with the brain are expressed by the body. Research has been done with the brain to determine the nature of the brain's control over the body and efforts have been made to interpret the signals in the brain with the hopes of controlling functions outside of the body. To this end, brain computer interfaces have been postulated.

A brain computer interface is an interface which receives information originating in the brain and transforms it into computer commands. A further definition may be an interface that accepts voluntary commands from the brain of a patient or specimen without requiring muscle movement. Brain computer interfaces have been the subject of several studies with mixed results. Early attempts at brain computer interfaces have included invasive methods of capturing voluntary signals from the brain of a specimen or patient. For example, electrodes have been placed in activity centers in the brain and based on that activity, computers or other devices have monitored those signals. Those signals can be converted into controls for computing devices. Invasive methods, however, have many shortcomings because they involve complex surgery or may otherwise pose unacceptable risk. In addition, these invasive methods tend to be incorporated into many single unit recording devices such as Electrocortincography.

Other invasive methods include, for example Positron Emission Tomography, where radioactive tracing elements are inserted into the blood stream of a patient. The gamma radiation emanating from the radioactive material may provide an image of the brain and may be used in one or more ways to measure brain activity and receive signals.

Non-invasive methods of measuring brain activity have also been considered. For example, Electroencephalography (EEG) provides several electrodes on the scalp of an individual and the summation of the firing of many neurons in the brain may be detected by the EEG.

More recently, the use of near infrared spectroscopy has been considered as a non-invasive way to measure brain activation. Near infrared spectroscopy has been used in human brain activation studies as a method for non-invasively assessing oxygenation changes in the brain. A light source emitting at least in part in the near infrared rang of the electromagnetic spectrum is positioned on the scalp of a patient and the photons that enter the tissue are either absorbed or scattered. A detector monitors the tissue. A percentage of the photons follow a relatively well-described pathway back to the surface of the scalp, where they can be measured with the detector. Different types of tissue and associated attributes of the tissue may cause changes in the absorption and/or scattering of the photons as they pass through the tissue. This technique allows calculation of changes in the oxyhemoglobin and deoxyhemoglobin rates in the tissue, which makes functional neuroimaging possible based on the information received at the detector.

Brain activity measurement has been considered for use as a controller of devices. However, the studies in this area have focused on, for example, Broca's region (a language processing region of the brain), providing a binary option for controlling a computer based on the word 'yes' vs. the word 'no.' In such an example, control of a computing device may be related to brain activity, but the activity is intended to control language, and is picked off in an ancillary manner and applied to computing.

SUMMARY

There are many problems associated with providing control over computer functionality using signals from the brain. One of those problems includes training individuals to actively up-regulate or down-regulate brain activity in such a way that a sensing device may detect the change in brain activity. A related issue is to determine if up-regulation and down-regulation of biomarkers can be volitional acts at all. Another problem is to properly correlate changes in brain activity with computing functions, and to do so in a non-invasive way. A further problem is finding, isolating and measuring biomarkers that may act as suitable brain computer interface indicators. An additional problem is selecting a region or regions of the brain that have the capacity for brain computer interfaces and that can be controlled at will by a person. Finally, a problem exists because prior art brain computer interfaces have relied on motor control function to control essentially unrelated computing tasks. This final problem is exemplified by the work previously done in monitoring brain activity that has focused on regions of the brain that control specific functions. For example, when a test subject performs a specific function, such as raising their arm, it is known that activation in a part of the brain related to motor control will occur. The brain activation for raising their arm may then be detected and used in a brain computer interface.

As a further example of correlating a motor control function with a computer command, previous experimentation has been performed on Broca's region of the brain, which is a language processing region of the brain. The experiment involved monitoring this region, and when the test subject spoke a word, such as, for example, 'yes', the output was distinct and could be correlated with a first binary computer output. If, however, a person spoke gibberish, the brain activity could be monitored and correlated with a different binary computer output. Again, monitoring brain activity in this region required specific overt action by the person unrelated to the computing function and that overt action was correlated with, in this instance, activity in Broca's region. Such experiments may also work if an individual merely visualizes moving the word, thus recreating the signal in the brain, which may be used by a computing device in one or more ways. In general, however, these experiments have not been done in real time, have not utilized functional near infrared (fNIR), and have measured bulk oxygenated hemoglobin and deoxygenated hemoglobin levels. The present disclosure provides solutions to some of the above problems.

The present disclosure addresses some of the problems noted above. In one embodiment of the present disclosure, fNIR can detect and output information related to oxygenated hemoglobin and deoxygenated hemoglobin individually. To further explain this, previous methods have made use of the combined bulk oxygenated hemoglobin and deoxygenated hemoglobin levels. Here, however, fNIR can be utilized to separate out, as specific biomarkers, oxygenated hemoglobin and deoxygenated hemoglobin individually. In another embodiment, fNIR may be used to detect an event related optical signal (EROS), which may be used to directly detect changes in the optical properties of the cell walls that occur as a function of depolarization during neural activation in real time detection.

Disclosed herein are functional near infrared based brain computer interfaces that may be used to train and test subjects to up-regulate and/or down-regulate neural activity and the related markers in the brain. More specifically, test subjects may be trained to control neural activity in specific regions of the brain, resulting in up-regulation or down-regulation of deoxygenated hemoglobins and/or oxygenated hemoglobin, and/or direct changes in the event related optical signal (EROS). This change in the biomarkers in the brain is not necessarily related to a motor control function of the brain, such as moving one's arm, performing a calculation or speaking a word. Rather, a user can be trained on a system to alter a condition (level of oxygenation) in a portion of their brain through biofeedback information regarding the level of oxygenation or neural activity in that portion of the brain.

In one embodiment, using fNIR and training, a user may be provided a binary control in a computing environment using a brain control interface. For example, a user may be coupled to a fNIR device that measures a biomarker in a portion of their brain. By up regulating or down regulating the biomarker, a threshold may be passed thereby providing a 0 or 1 for binary control. Thus, a brain interface may be provided for binary control of a computing device. Alternatively, a user may be provided a two or three dimensional control in a computing environment by using several areas of the brain to control, for example, up-down, left-right directions and a selection function (e.g., the equivalent of a mouse "click."

In another embodiment, a user may be provided continuous control in a computing environment, or over an object using a brain interface control. For example, a user may be coupled to an fNIR device that measures a biomarker in a portion of the brain. By up regulating or down regulating the neural activity and/or a biomarker, a continuous action may track the regulation. For example, a brain computer interface can be provided where a baseline level of the biomarker is indicative of a full stop of, for example, a virtual car, and an increase in the biomarker causes the virtual car to speed up in relation to the amount of the biomarker in the portion of the brain being measured.

Also disclosed herein is a brain computer index for determining a scale indicative of the change in biomarkers in the brain. In one embodiment, a test subject may have a fNIR brain computer interface placed in association with their brain. One or more biomarkers such as deoxygenated hemoglobin and/or oxygenated hemoglobin and/or EROS may be measured, monitored, stored or otherwise determined by the fNIR brain based computer interface. A feedback stimulus may then be provided to the person. In one embodiment, the feedback may be in the form of a visual display auditory, or haptic signal. At the point in time that the feedback stimulus is provided to the subject, the level of the biomarker in the monitored region of the brain may be determined. One or more algorithms may be used to correlate this reference point with a biomarker scale. The biomarker scale may then be used to determine an expected threshold level in, for example, a binary brain control interface. The biomarker scale may also be used in, for example, a continuous brain control interface and may correlate an amount of change in the biomarker with an amount of change in the continuously controlled computing function.

Disclosed herein is a functional near infrared based brain measures for personalized therapy. In one embodiment, a person may be trained to alter and regulate neural activity and biomarkers, such as oxygenated hemoglobin and/or deoxygenated hemoglobin and/or the EROS and in the cortical region of the brain. Further, a person may be trained to regulate, increase, decrease or otherwise alter these biomarkers in regions of the brain specific to particular functions, such as, for example, memory, concentration, pain avoidance, self control, or any other known functions. Once a person is trained to alter the biomarkers, the regulation can be utilized as a regular part of therapy.

Also disclosed herein is a functional near infrared brain based personalized learning system. In one embodiment, a person may utilize a cortical fNIR monitoring system to regulate biomarkers such as oxygenated hemoglobin and deoxygenated hemoglobin in a region of the brain related to learning. The person may then be able to apply the ability to regulate the region of the brain during specific tasks such as, for example, learning. This may lead to an increase in the capability of learning by the individual.

In one embodiment, one or more near infrared emitters may emit near infrared radiation on a portion of a cortical region. The radiation may be absorbed, transmitted, or backscattered by various tissues associated with the cortical region. One or more detectors receive the backscattered radiation from the portion of the cortical region. The amount and types of radiation is associated with the event related optical signal and/or the amount of oxygenated hemoglobin and the amount of deoxygenated hemoglobin and oxygenated hemoglobin in the portion of the cortical region. The test subject may be provided feedback based on the neural activity and/or amounts of deoxygenated hemoglobin and oxygenated hemoglobin. By monitoring the feedback, a test subject may be trained to up-regulate or down-regulate the activation of the cortical region.

In another embodiment, a computing device may also receive information related to the biomarkers such as the amount of oxygenated hemoglobin and/or the amount of deoxygenated hemoglobin and/or EROS in the test subject's cortical region and may associate one or more computing instructions with the information. As a first example, control over a three dimensional space, such as a gaming environment may incorporate aspects of computer brain computer interface to control one or more elements of the game.

In another embodiment, a fNIR system may detect oxygenation levels in one or more portions of the cortical region and a user may be provided information reinforcing a change in the oxygenation level of the portion of the cortical region, wherein the change is representative of an up-regulation and/or down-regulation of deoxygenated hemoglobin and/or oxygenated hemoglobin in the specific portion of the cortical region.

BRIEF DESCRIPTION OF THE DRAWINGS

FIGS. 1(a), 1(b) and 1(c) depict an example of a fNIR method for monitoring a person's brain.

DETAILED DESCRIPTION OF ILLUSTRATIVE EMBODIMENTS

As described herein, brain computer interfaces may be applied to any region in the brain. It should be noted that the present disclosure applies also to the entire cortical region, cortex, the prefrontal cortex, the dorsolateral prefrontal cortex, and the ventrolateral prefrontal cortex. It is envisioned that the brain can be monitored and feedback may be provided to a user in many regions of the brain, including but not limited to the cortical region, the cortex, prefrontal cortex, the dorsolateral prefrontal cortex, the motor control regions of the brain, Broca's region, or any other portion. It should further be noted that portions of the prefrontal cortex have been divided into International 10-20 sites, as well as Brodmann's areas, and arbitrarily assigned voxels, each of which may be considered regions defined for the purpose of disclosure, several of which may be in the prefrontal cortex. Any region of the brain that may be interrogated using fNIR may be considered as a region for implementing training, up-regulating, down-regulating and as an area for providing feedback based on oxygenation levels. Further, the training, up-regulating, down-regulating and providing feedback can be applied to other, deeper sensing mechanisms in brain based technology.

FIGS. 1(a)-(c) depict an example of a functional near infrared (fNIR) system for monitoring a person's brain, or more specifically, a portion of the cortical region. In one embodiment of the present invention, fNIR is used in a brain computer interface as a non-invasive method for studying functional activation of the brain by monitoring changes in the hemodynamic properties and is based on the intrinsic optical absorption of both deoxygenated hemoglobin (DH) and oxygenated hemoglobin (OH). fNIR has the ability to simultaneously measure the concentration changes of deoxy-hemoglobin, oxy-hemoglobin and thus total hemoglobin. In addition, the signal processing time of fNIR is less than other methods, such as fMRI, so fNIR data can be processed in real time. Accordingly, feedback can be provided based on fNIR methods in real time.

Figure 2:
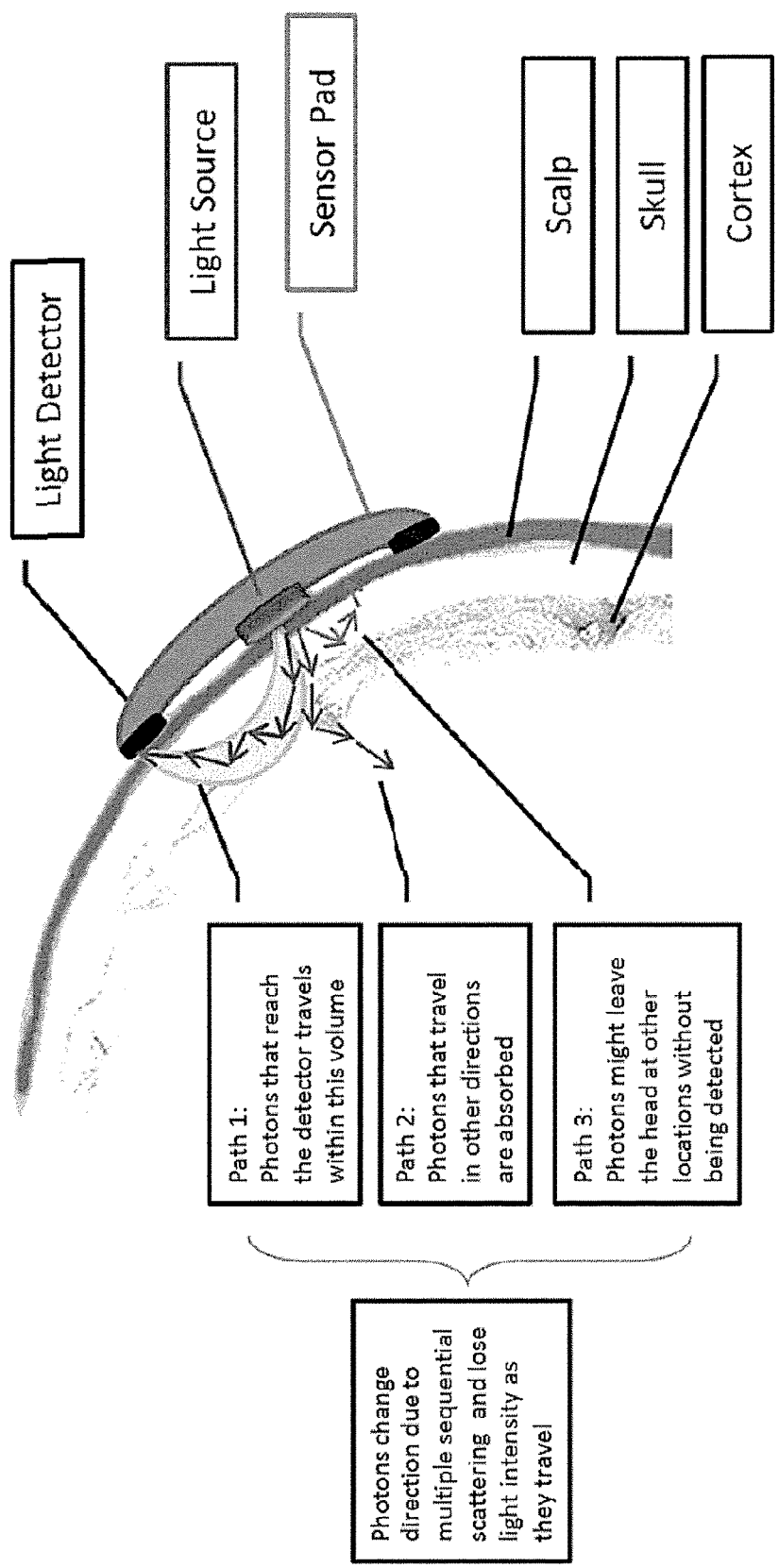
FIG. 2 depicts a further example of fNIR including several possible photon paths.

FIG. 2 is another depiction of fNIR and the light path that fNIR may take in passing through tissue in the brain of a test subject. Although not limiting, an example experimental description of fNIR is now included. Typically, an optical apparatus for fNIR Spectroscopy consists of at least one light source that shines light to the head and a light detector that receives light after it has interacted with the tissue. Photons that enter tissue undergo two different types of interaction: absorption and scattering. Primarily, most part of biological tissue (including water) is relatively transparent to light in the near infrared range between 700 to 900 nm, largely because water, a major component of most tissues, absorbs very little energy at these wavelengths. Moreover, the hemoglobin molecule is the dominant chromophore (light absorbing molecule) in this range of the spectrum. This spectral band is often referred to as the 'optical window' for the non-invasive assessment of brain activation. Absorption characteristics of dominant chromophores according to light indicates and optical window between 700 nm to 900 nm.

There is an ever growing body of evidence that deoxy-hemoglobin (deoxy-Hb) and oxyhemoglobin (oxy-Hb) are correlates of brain activation by oxygen consumption of neurons thus, oxy- and deoxy-Hb, are strongly linked to tissue oxygenation and metabolism. Fortuitously, the absorption spectra of oxy- and deoxy-Hb remain significantly different from each other allowing spectroscopic separation of these compounds to be possible by using only a few sample wavelengths. Once the photons are introduced into the human head, they are either scattered by extra- and intracellular boundaries of different layers of the head (skin, skull, cerebrospinal fluid, brain tissue, and so forth) or absorbed mainly by oxy- and deoxy-Hb. If a photodetector is placed on the skin surface at a certain distance from the light source, it can collect the photons that are scattered and thus have traveled along a "banana shaped path" from the source to the detector.

In one embodiment, the fNIR device may be a continuous wave system. In other embodiments, it may comprise a time resolved and/or frequency domain system.

Figure 3A:
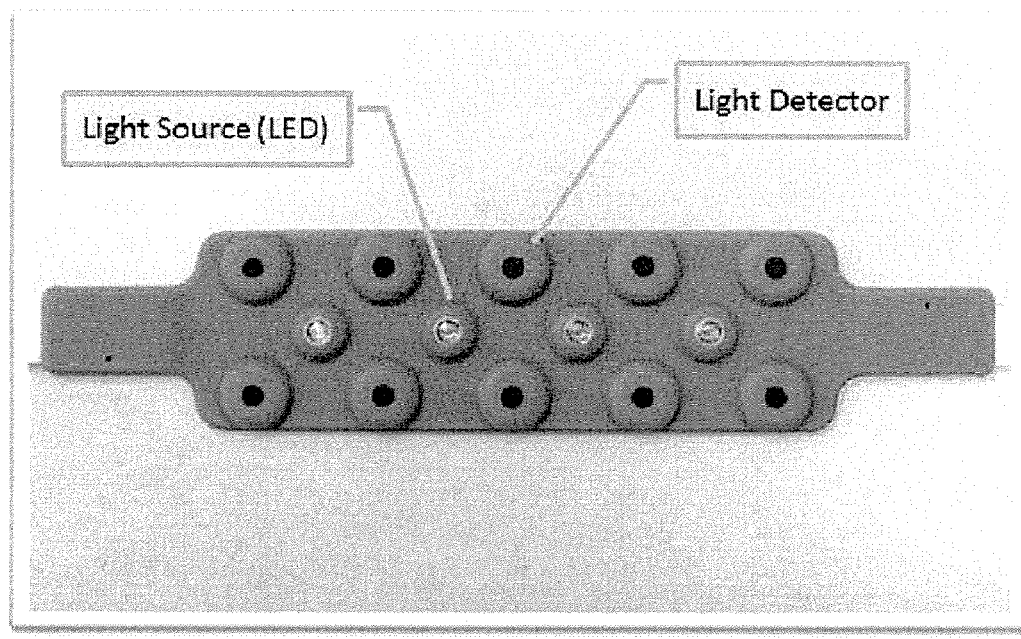
FIGS. 3(a) and 3(b) depicts an experimental setup using a headband with both NIR emitters and detectors and attaching the experimental setup to the forehead of a test subject.
Figure 3B:

FIG. 3 depicts an fNIR headband used in an experimental setup. In one embodiment, the fNIR brain computer interface may comprise a flexible headband comprising elements such as emitters, sensors, A/D converters, noise reduction elements, gyroscopes, accelerometers, other signal processing circuitry and/or a control unit. In another embodiment, it may be a rigid hat or helmet, a semiflexible band or the like. In general, the configuration of the fNIR brain computing interface should be such that an emitter may provide infrared radiation to the head of a test subject and such that a detector may receive information from the head of the test subject. While there is envisioned a single unit comprising both emitters and detectors, such a configuration is not necessary and each emitter and detector could be attached individually, in groups, in a hat, in a band, in a helmet or in any other way known in the art. In addition, the control unit and/or other elements may be included in the headband, hat or helmet, or it may be a stand alone unit and attached wirelessly or via wires to the other elements of the brain computer interface.

In an embodiment, the headband unit may contain one or more light emitting devices, diodes, lasers, bulbs, light or the like. It may also comprise one or more detectors capable of detecting at various wavelengths in the near infrared portion of the electromagnetic spectrum. The detectors may be of any type known in the art including, but not limited to, photodiodes, CMOS, CCD devices, or any other type of detector known in the art. In a further embodiment, the light sources and detectors may be configured to have peak emission and detection at around 730 nm and/or 850 nm, or other wavelengths within the near infrared portion of the electromagnetic spectrum. As one example, multiple wavelengths may be used such that the different absorption spectra of OH and DH can be distinguished from each other.

In another embodiment, Event Related Optical Signals techniques may be used instead of, or in combination with the oxygenated hemoglobin and the deoxygenated hemoglobin. In such an example, one or more optical emitters and detectors may be configured to directly measure changes in the EROS signal to determine the firing rates of particular neurons or regions of the brain. Oxygenation of the brain may include a secondary effect of neural activity and firing, and measuring EROS may provide a more direct and precise manner of detecting and determining brain activity by measuring changes in the spectra of light being emitted from firing neurons. As such, for each of the embodiments described herein, optical instruments may be used to determine the EROS instead of or in combination with the oxygenation levels to provide for a brain interface control.

As can be seen in FIGS. 1, and 2, the light source is at some angle to the forehead of a test subject which may result in a curved path for near infrared radiation. Thus the placement of the emitter and detectors may be configured such that brain imaging, and more specifically, biomarker imaging related to the oxygenated hemoglobin and the deoxygenated hemoglobin may occur.

In an embodiment, fNIR brain monitoring technology is used in brain computer interfaces. For example, an fNIR device may receive information from a person's brain indicating the levels of one or more of DH and OH. As a first example, these levels can be monitored, tracked, recorded and displayed in any manner known in the art. Further, the DH and OH may be individually determined and monitored, thereby providing more information that some of the prior art which relied on, or only determined the bulk concentration of both oxygenated hemoglobin and deoxygenated hemoglobin. Further to this point the detector and computer device described above may be able to detect various wavelengths of light and from that data may be able to unravel both the OH and the DH levels individually. As such, the individual OH level can be monitored, stored, tracked or used in any other way in a brain computer interface independent of the DH. By the same token, the DH can be monitored, stored, tracked or used in any other way in a brain computer interface independently of the OH.

In an embodiment, feedback may be provided to a person that is having their brain, or more specifically cortical region monitored. The person can then be instructed to attempt to alter the feedback in one or more ways. By attempting to alter the feedback and being able to receive real time updates indicating whether or not the feedback is being altered, a person may learn to effectively alter the feedback at will, which in turn would mean that a person has learned to alter the DH and OH levels in at least a portion of their cortical region.

Figure 4A:
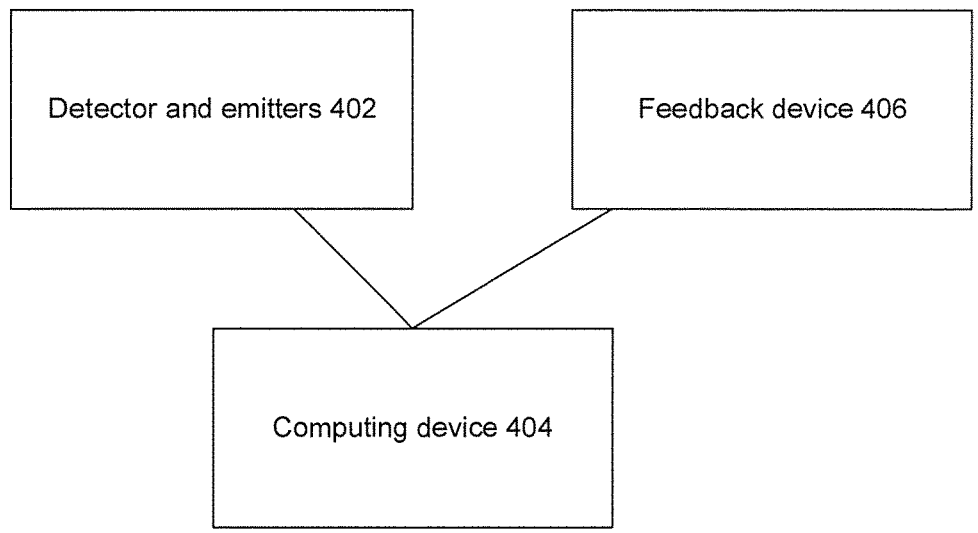
FIG. 4(a) depicts an example setup of an fNIR brain control interface and 4(b) depicts an example of a feedback mechanism in a rest and task state, where the feedback mechanism in task state represents an aspect of a biomarker of a test subject.

FIG. 4(a) depicts an example of an experimental setup including fNIR, a computing device and a feedback mechanism. The fNIR system 402 may be the fNIR system described above with respect to FIGS. 1, 2 and 3. The computing device 404 may be a computing device comprising one or more processors, memories, disks, drives, I/O devices and the like. The computing device may control the operation of the fNIR 402 and may receive information from fNIR 402. Information received from fNIR 402 may be converted as necessary and may be interpreted in one or more way to, for example, determine OH and DH levels, and or to provide feedback to a person.

The computing device may also include signal processing controls that may be used in one or more ways to isolate signals using the information received from, for example, the fNIR 402 detectors. The signal processing controls may be used to remove noise based on other brain activity, or it may be used to remove noise based on motion of the test subjects head, external light sources and the like. In one embodiment, the fNIR device may include a gyroscope or an accelerometer which may be correlated with data received from the detectors to remove noise based on motion of a test subject.

At 404, feedback may be provided on a feedback device. The feedback device may be a display, including but not limited to a television, a computer monitor, a touch screen, a projector or any other type of display known in the art. The feedback may also be in the form of audible feedback provided to a person, heat, pain, touch or any other manner of feedback known in the art. The feedback is related to the information received by fNIR 402 and process by computing device 404 and may be used in the training of a person to up-regulate OH and DH levels in a portion of the cortical region, and may also be used in training a person to operate a computing device using a brain computer interface.

Figure 4B:
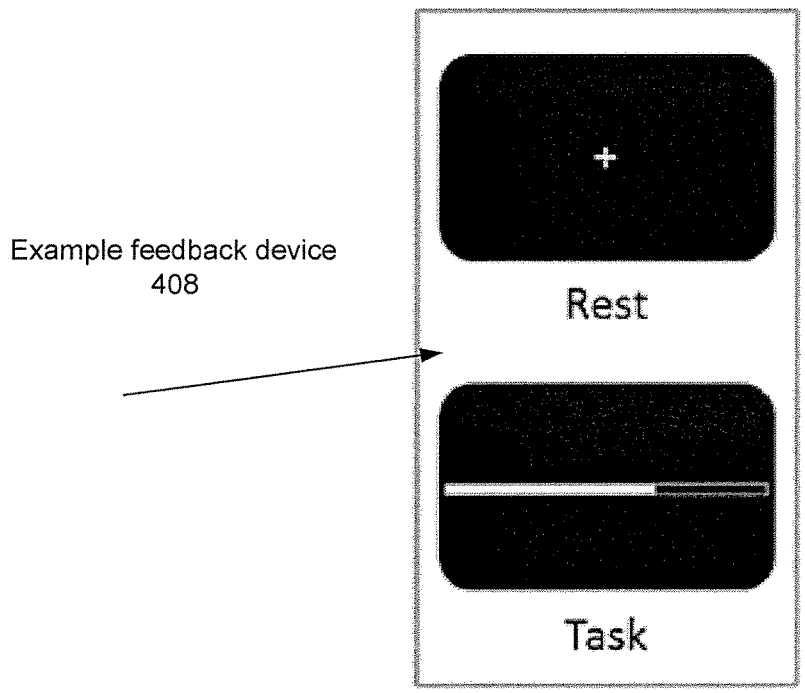

FIG. 4(b) depicts an example of a continuous feedback display. In one embodiment, a test subject is told to rest and shown the rest screen. The test subject may then be shown the bar graph of FIG. 4(b) initially in an empty state (not shown). As the user increases the amount of, for example, oxygenated hemoglobin or deoxygenated hemoglobin in the brain, the bar may fill proportionally. Accordingly, a continuous control over a computing element may be provided using a brain computer interface and therefore the person may also maintain continuous control over the feedback and the amount of DH and/or OH in the measured portion of the brain.

In FIG. 4(b), the specific task was lengthening a bar in a continuous manner. This is merely one example of continuous control and many others exist. For example, any function that may be controlled by a computing device in a continuous manner may be controlled continuously using the DH and OH levels using a brain computer interface. As an example, motion of an object, location, speed, acceleration, computer control of a mechanical device such as a mechanical arm or limb, or any other type of control having a continuous spectrum may be controlled using the brain control interface.

Although FIG. 4(b) depicts a continuous control, it is not necessary that the control be continuous. It is also possible to provide binary or step control over computing functions based on one or more threshold levels of DH and OH in a monitored region of the cortical region. For example, a binary 0 may be attributed to DH and/or OH levels below a certain point and a binary 1 when DH and/or OH levels above a certain point. Further, any number of threshold points may be attributed to DH and/or OH levels in a portion of the cortical region.

It will be understood by one having ordinary skill in the art that a person may be provided feedback about the neural activity via EROS or oxygenation levels in a portion of their brain, and simultaneously, they may be able to control a computing function with the neural activity, OH and DH levels in the portion of the brain. In one embodiment, a computer function may be any computer function at all, including a yes/no response to a question provided to a user. A 0 or 1 binary input related to any aspect of software, hardware or circuitry, or any other computing function. It will be further understood that while feedback may be provided simultaneous with binary or continuous control over a computing function, the feedback is not necessary. For example, in another embodiment, a person may have been trained to up-regulate and/or down-regulate OH, and DH levels in one or more portions of the brain and then may be able to control in a binary or continuous fashion a computing function without feedback. In a further embodiment, the person may be able to up-regulate and/or down-regulate neural activity, HbO and HbR levels without feedback and without controlling a computer at all, yet the regulation may provide therapeutic benefits if a person learns to control this functionality.

Each individual may have a different base line for a particular biomarker, and each person may have maximums or hemodynamic response times. Accordingly, in one embodiment, a brain computer interface index is used to account for the differences in chemistry and physiology associated with each individual. A non-limiting experimental example of this is included below.

In an embodiment, data was performed at real-time during an experiment in order to calculate the oxygenation changes in the prefrontal cortex of a subject at real-time and to generate visual feedback. First, the raw optical intensity values in two NIR wavelengths (730 nm and 850 nm) at each sampling instance (that were sampled by the COBI Studio) were received through TCP/IP protocol at 2 Hz frequency. Next, modified beer lambert law was applied to calculate oxy- and dexoy-Hb concentration changes. The rest and task period beginning and end time information was utilized at real-time to identify if the received optical data is part of a rest period or if in task period, oxygenation values were used to generate a feedback index.

Oxygenation changes during task periods (based on respective rest period) was used to calculate a bar size (visual cue of FIG. 4) and update the visual display accordingly. Size of the bar was modeled as a linear transformation of the oxygenation changes of channel 6 that corresponds to a voxel location close to Fp1 in the international 10-20 system. Bar size was employed to deliver feedback about regional brain activity with respect to the beginning of the task.

Let Bar(t) represent the bar size (in screen pixels) at time t, and t0 is the beginning time of the task period when first sample is received just after rest period (Equation 4.1). Let OxyHb(t) and Deoxy-Hb(t) represent the oxy-Hb and dexoy-Hb concentration changes at time t. Let 'Width' signify the screen width, which is the maximum possible bar size in screen pixels.

BaseMin(t) is the moving average of the last k oxygenation changes (oxy-Hb and dexoy -Hb difference) scaled by a constant (1−α) at time t (Equation 4.2). BaseMin function basically, indicates the target oxygenation level when bar size is at minimum level. Similarly, if the scaling constant is (1+α), that would indicated the target oxygenation level for maximum bar level. Thus, the range of the bar is the BarRange function as shown in (Equation 4.3, with a scaling coefficient of 2α. (Equation 4.1 essentially indicates that bar size at any time t is calculated by the difference of the current oxygenation to the initial target minimum divided by the target range. So, by using k=1 and α=1.5, at time t0 the bar size would is 50%; that is the half the screen width. The parameter α is a conversion parameter that selects how sensitive bar movement is to the oxygenation changes. Selecting large values would make the target BarRange larger and thus, much larger oxygenation changes would be required to complete the bar task. In the current study, α=1.5 was used for all subjects.

$$\text{Bar}(t) = \frac{OxyHb(t) - DeoxyHb(t) - BarMin(t_0)}{BarRange(t_0)} * \text{Width} \quad \text{(EQUATION 4.1)}$$

$$BarMin(t) = \frac{1-\alpha}{k}\sum_{i=1}^{k}(OxyHb(t-i) - DeoxyHb(t-i)) \quad \text{(EQUATION 4.2)}$$

$$BarRange(t) = \frac{2\alpha}{k}\sum_{i=1}^{k}(OxyHb(t-i) - DeoxyHb(t-i)) \quad \text{(EQUATION 4.3)}$$

Figure 5:
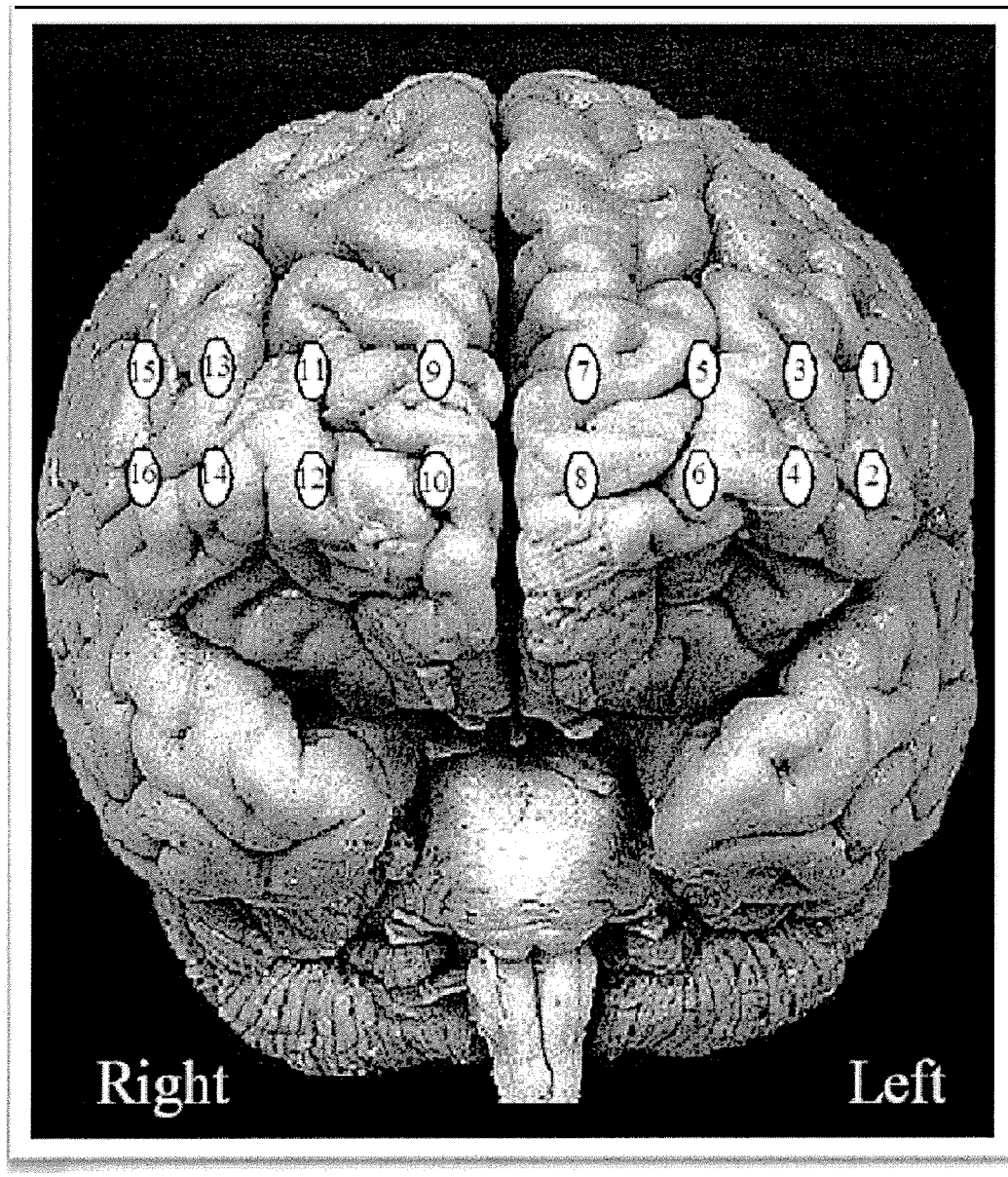
FIG. 5 depicts a picture of a human brain with number regions, each depicting a voxel, labeled 1-16.

FIG. 5 depicts a brain having a series of regions or voxels depicted on the prefrontal cortex which relate to the placement of fNIR source-detector pairs. Voxel placement is typically described in relation to the International 10-20 method of placement, or in terms of underlying Brodmann areas. Voxel names or numbers are therefore arbitrary, relative to any given study. In an embodiment, a first voxel may be selected for use in a fNIR brain control interface. For example, although the headband discussed above with respect to FIG. 4 may be able to measure the output from all 16 voxels in FIG. 6, a person may be provided feedback on only one voxel, or on two, or on any number of voxels. Accordingly, a person may be trained to up-regulate DH and/or OH in a particular localized region of the brain.

In an experimental example, the levels of DH and OH were measured using fNIR in voxel 6 as defined in FIG. 5 placed adjacent to Fp1/AF7 of a number of test subjects. The subjects each had the fNIR device attached, and were shown the feedback depicted in FIG. 4. The feedback was based on the DH and OH levels in voxel 6. Each of the individuals provided feedback of the DH and OH level in voxel 6 was trained to up-regulate the DH and OH levels in that particular voxel. In addition, the up regulation was localized to a large degree, meaning that the amount of up regulation in voxel 6 had the most significant amount of change and the change did not carry over to the other voxels. Experimental results of this are provided in FIGS. 6, and 7.

Figure 6:
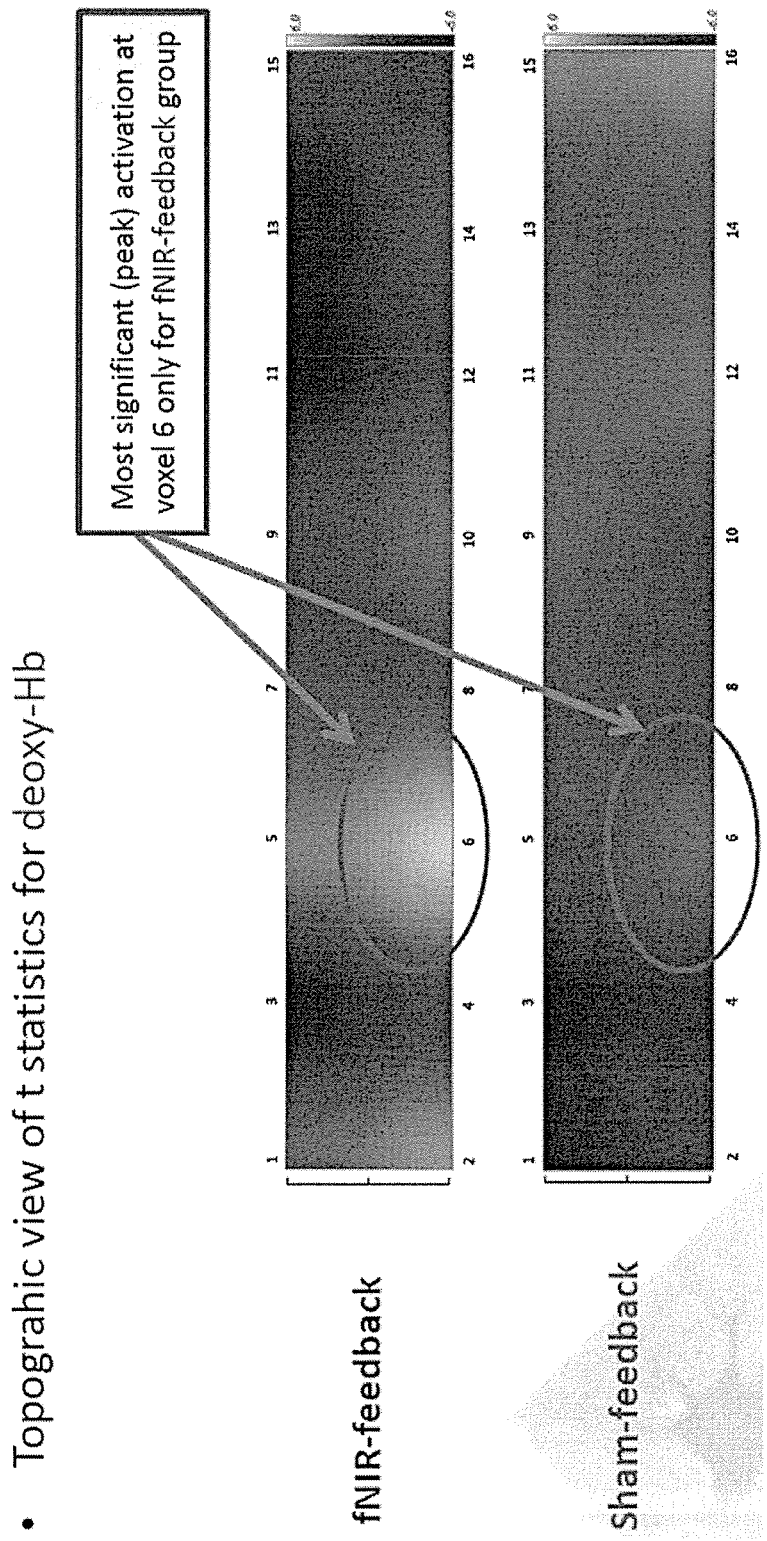
FIG. 6 depicts an experimental result where a test subject was provided feedback based on biomarkers in voxel 6 of the prefrontal cortex depicted in FIG. 5.

FIG. 6 depicts an experimental result where a test subject was provided feedback based on biomarkers in voxel 6, of the prefrontal cortex depicted in FIG. 5. As can be seen, the region of the brain associated with voxel 6 has the highest levels of DH and OH in the prefrontal cortex. In addition, a rest state of the brain of the test subject is shown, but because feedback was provided from voxel 6, the prefrontal cortex learned to up-regulate the DH and OH in that localized portion of the brain.

Figure 7:
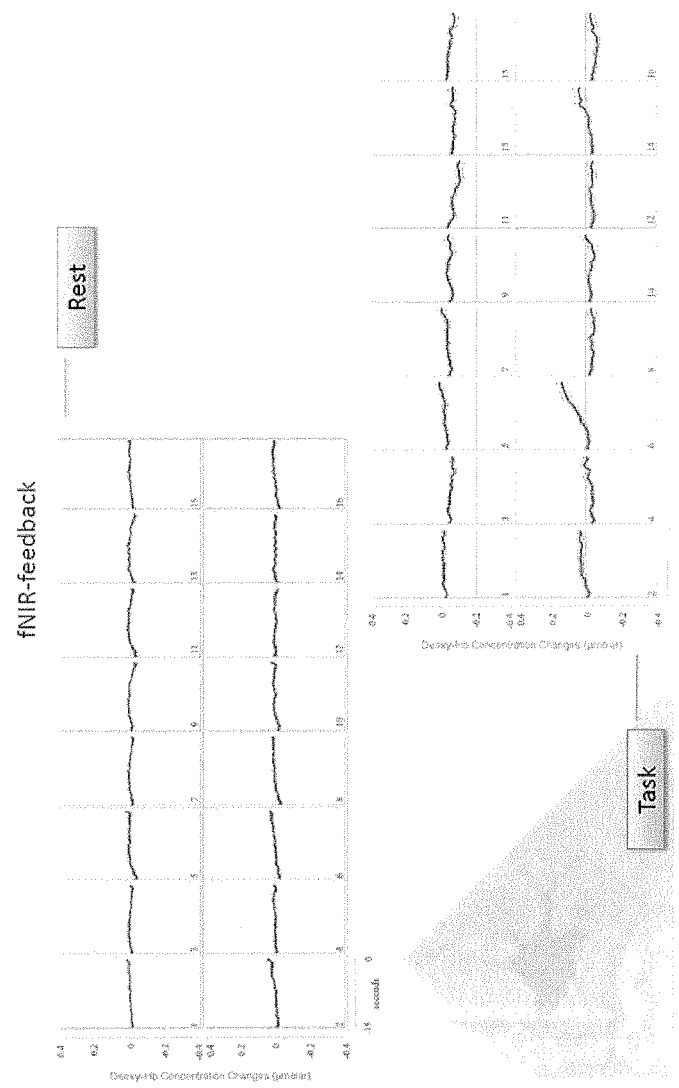
FIG. 7 depicts experimental results from each of the 16 voxels depicted in FIG. 5 showing a rest and a task state for a test subject.

FIG. 7 depicts experimental results from each of the 16 voxels depicted in FIG. 5 showing a rest and a task state for a test subject. At rest, it can be seen that the concentration of DH is steady or nearly steady across each of the voxels. Upon providing a test subject with the bar graph and instructing them to fill it, test subject effort results in an increase in the concentration levels of DH which indicates a significant, intentional increase in the oxygenation level.

Figure 8:
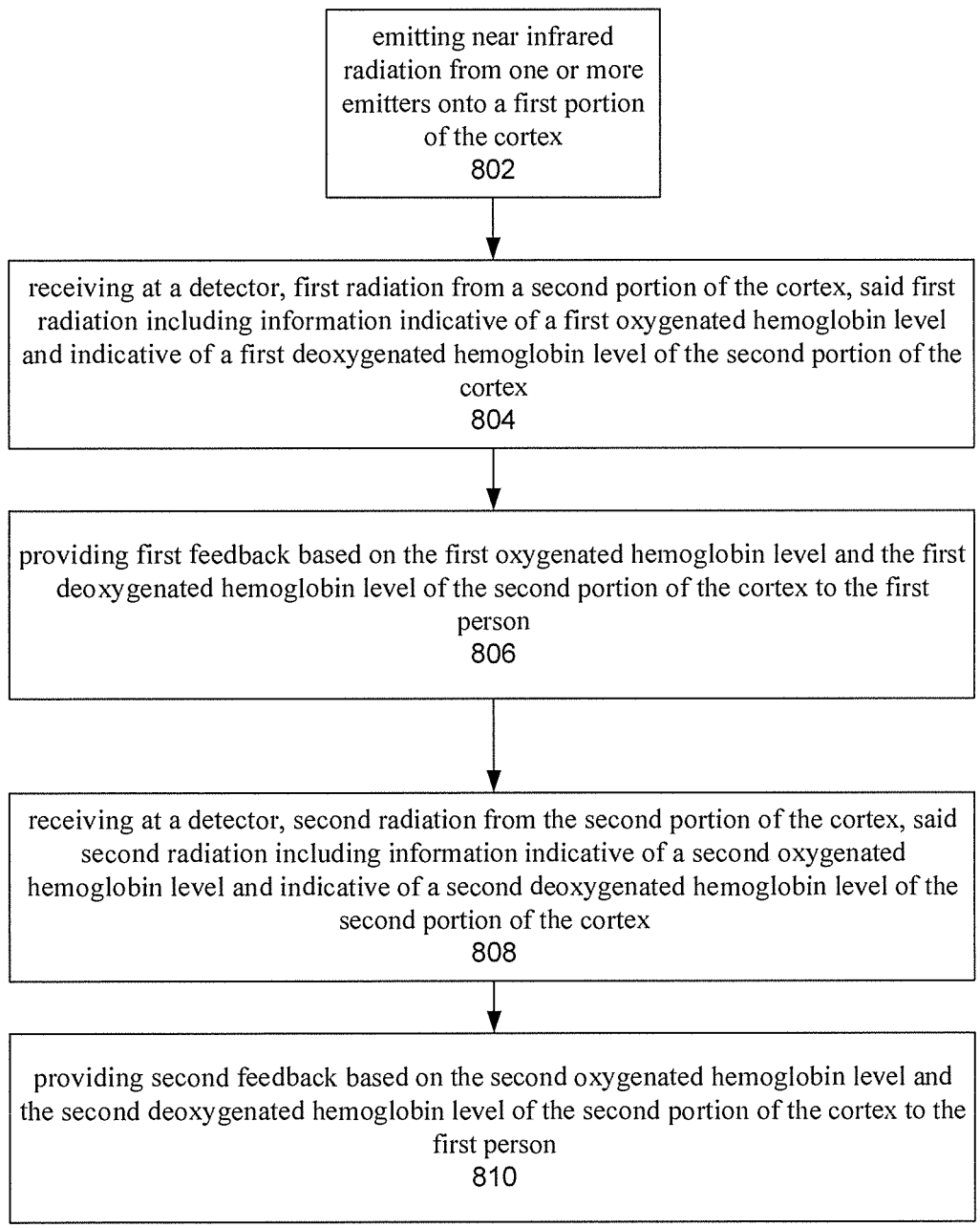
FIG. 8 depicts an example method for training a person to control a computer with a first portion of their cortex.

FIG. 8 depicts an example method for training a person to control a computer with a first portion of their prefrontal cortex. At step 802 the emitting near infrared radiation from one or more emitters onto the cortex may take place. As noted above, an emitter configured to emit on a portion of the cortex may be any emitter known in the art and may emit in the near infrared wavelength region. Furthermore, the emitter may emit across a broad range of wavelengths. The emitter may have peak wavelengths such that the penetration depth in tissue of the near infrared radiation may be at a peak, or such that the absorption, reflection, backscatter and the like of any biomarker may be at a peak or otherwise optimized.

In the embodiment described in FIG. 8, the light may be emitted on a first portion of the cortex. It should be understood that the first portion of the cortex may be any portion including but not limited to the brain, the entire cortex, the prefrontal cortex, one or more voxels, equal to the second portion or any other portion known in the art. With regard to the second portion of the cortex, the second portion may be any portion of the cortex including but not limited to the whole cortex, the prefrontal cortex, one or more voxels, the first portion or any other portion known in the art. Step 802 may include means for emitting near infrared radiation from one or more emitters onto a first portion of the cortex.

At step 804 first radiation from the second portion of the cortex may be received at a detector, the first radiation including information indicative of a first oxygenated hemoglobin level and indicative of a first deoxygenated hemoglobin level of the first portion of the prefrontal cortex. As noted above, the radiation received may be related to the near infrared radiation emitted at step 802. The radiation received at the detector may include radiation that is reflected, emitted, scattered or transmitted by or through any tissue, organ, interface or composition in the brain. In one embodiment, the information received may be indicative of the level of certain biomarkers, including but not limited to OH and DH. This information may be used in any number of ways, including but not limited to sending it to a computing device, providing feedback to a user, instructing a computing device and the like. Step 804 may include means for receiving at a detector, first radiation from a second portion of the cortices, said first radiation including information indicative of a first oxygenated hemoglobin level and indicative of a first deoxygenated hemoglobin level of the second portion of the cortex.

At step 806, first feedback may be provided to the person, the feedback based on the first oxygenated hemoglobin level and the first deoxygenated hemoglobin level of the portion of the prefrontal cortex. The feedback provided to the person may be in any form known in the art. For example, the feedback could be a display on a computer screen. In the experimental example noted above, the feedback was in the form of a continuous bar graph. The feedback could also be a binary display, or any other suitable representation. The feedback could also be audible, based on touch, heat, pain or any other sense. The feedback is related to the amount of OH and DH as determined by detecting the radiation from the prefrontal cortex and may be provided in a closed loop real time basis. Step 806 may include means for providing first feedback based on the first oxygenated hemoglobin level and the first deoxygenated hemoglobin level of the second portion of the cortex to the first person.

At step 808, second radiation from the second portion of the cortex, said second radiation including information indicative of a second oxygenated hemoglobin level and indicative of a second deoxygenated hemoglobin level of the second portion of the cortex. As noted above with respect to step 804, the radiation may be of any type providing an indication of DH and OH in the cortex. Step 808 may include means for receiving at a detector, second from the second portion of the cortex, said second radiation including information indicative of a second oxygenated hemoglobin level and indicative of a second deoxygenated hemoglobin level of the second portion of the cortex.

At step 810, second feedback can be provided to the person based on the second oxygenated hemoglobin level and the second deoxygenated hemoglobin level of the portion of the cortex. There is first and second feedback sent at different points in time, or, in one embodiment, in real time. Accordingly, a person would be able to tell if the levels of DH and OH were changing and how they are changing. Accordingly, a person can be trained to regulate these levels and change them at will with the feedback. Step 810 may include means for providing second feedback based on the second oxygenated hemoglobin level and the second deoxygenated hemoglobin level of the portion of the cortex to the first person.

Figure 9:
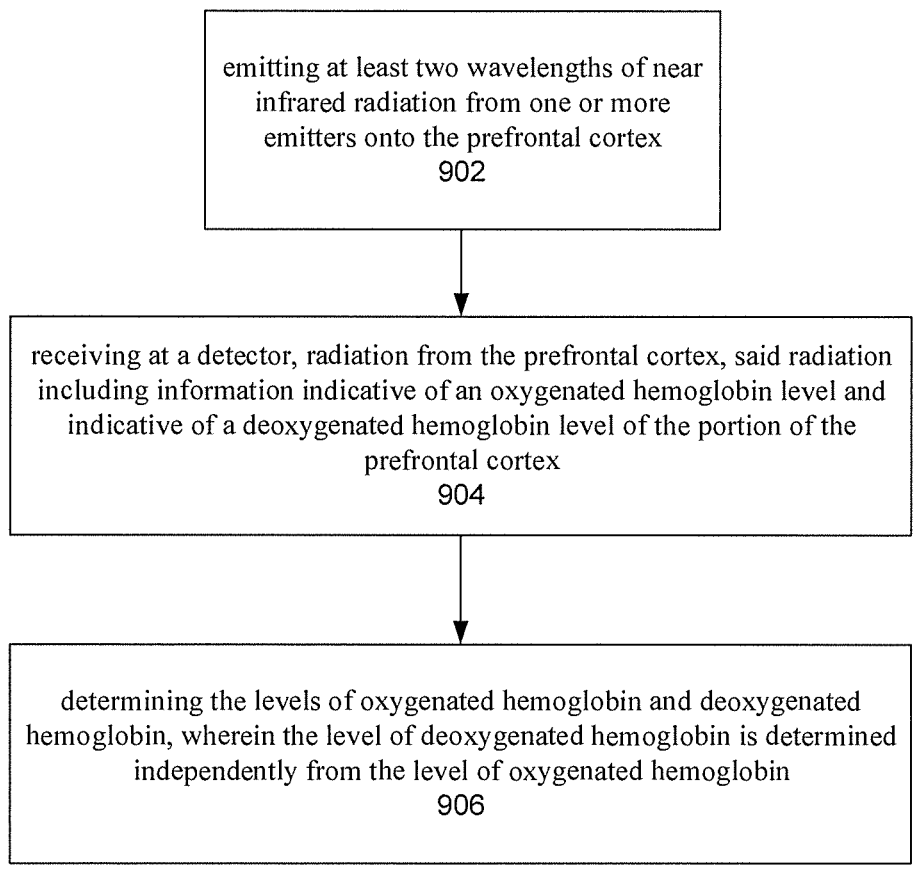
FIG. 9 depicts an example method for utilizing oxygenated hemoglobin and deoxygenated hemoglobin independently.

FIG. 9 depicts an example method for utilizing oxygenated hemoglobin and deoxygenated hemoglobin independently. In previous works, the indicators in hemodynamic studies have relied on bulk hemoglobin indicators. In one embodiment, fNIR may be used to distinguish the individual markers, thereby creating a more rich data set for determining properties of upregulation and the like.

At step 902, and emitter may emit at least two wavelengths of near infrared radiation from one or more emitters onto the prefrontal cortex. This may be any of the emitters noted above. Step 902 may comprise means for emitting at least two wavelengths of near infrared radiation from one or more emitters onto the prefrontal cortex.

At step 904, a detector may receive radiation from the cortex, said radiation including information indicative of an oxygenated hemoglobin level and indicative of a deoxygenated hemoglobin level of the portion of the cortex. As noted above the portion of the cortex may be any portion. Step 904 may comprise means for receiving at a detector, radiation from the cortex, said radiation including information indicative of an oxygenated hemoglobin level and indicative of a deoxygenated hemoglobin level of the portion of the cortex.

At step 906, levels of oxygenated hemoglobin and deoxygenated hemoglobin may be determined, wherein the level of deoxygenated hemoglobin is determined independently from the level of oxygenated hemoglobin. Here, the bulk hemoglobin, or the combination of both oxygenated hemoglobin and deoxygenated hemoglobin is not necessarily calculated. Instead, each of the biomarkers may be determined and used in any way to calculate other values, provide feedback and the like. Step 906 may comprise means for determining the levels of oxygenated hemoglobin and deoxygenated hemoglobin, wherein the level of deoxygenated hemoglobin is determined independently from the level of oxygenated hemoglobin.

With regard to each of the means for the various elements described above, they may be used in any combination without limitation. The various combinations may also include additional means for determining the EROS, means for determining neural activity and the like.

Figure 10:
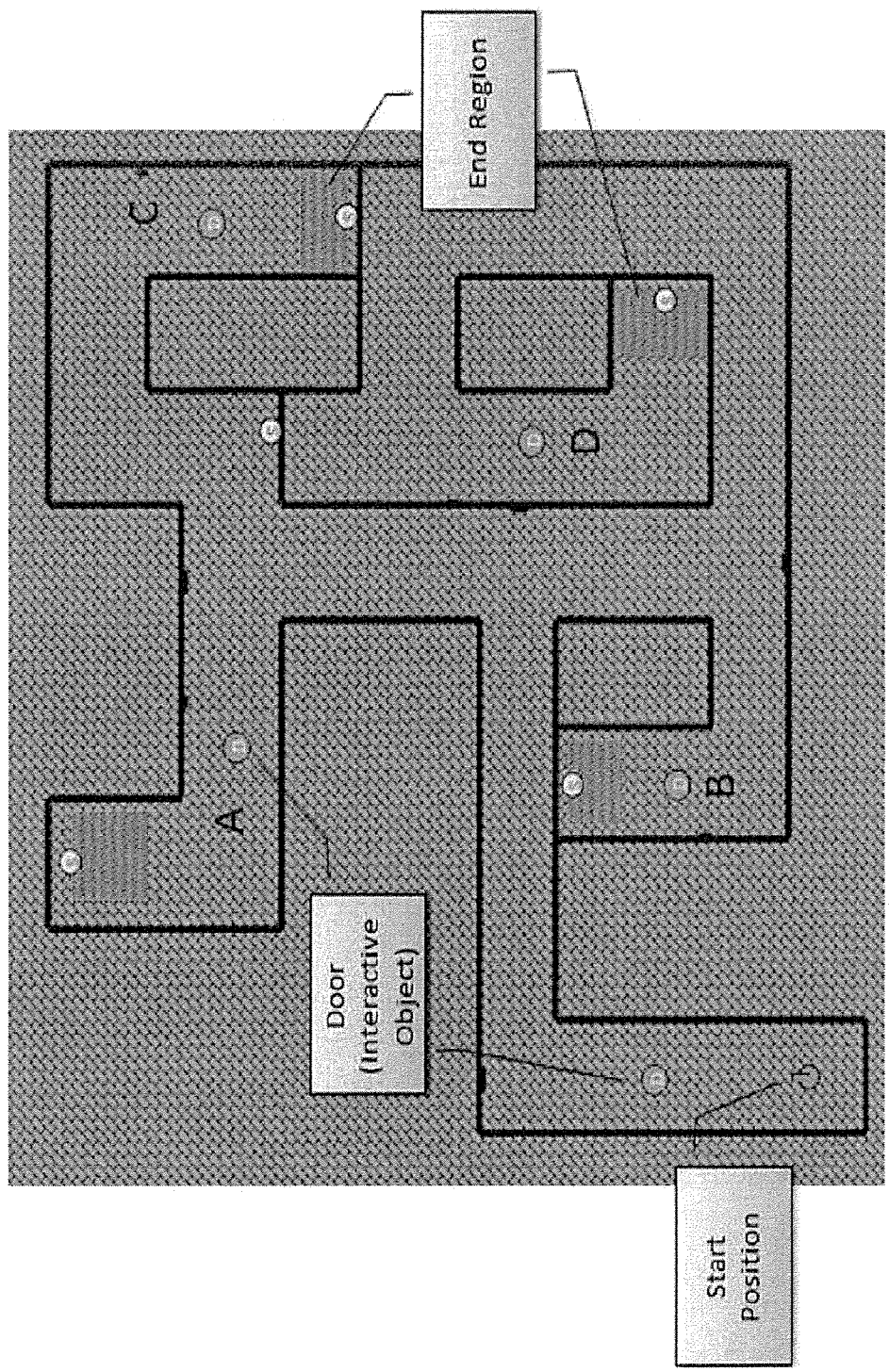
FIG. 10 depicts an example maze in a top down view as described below.
Figure 11:
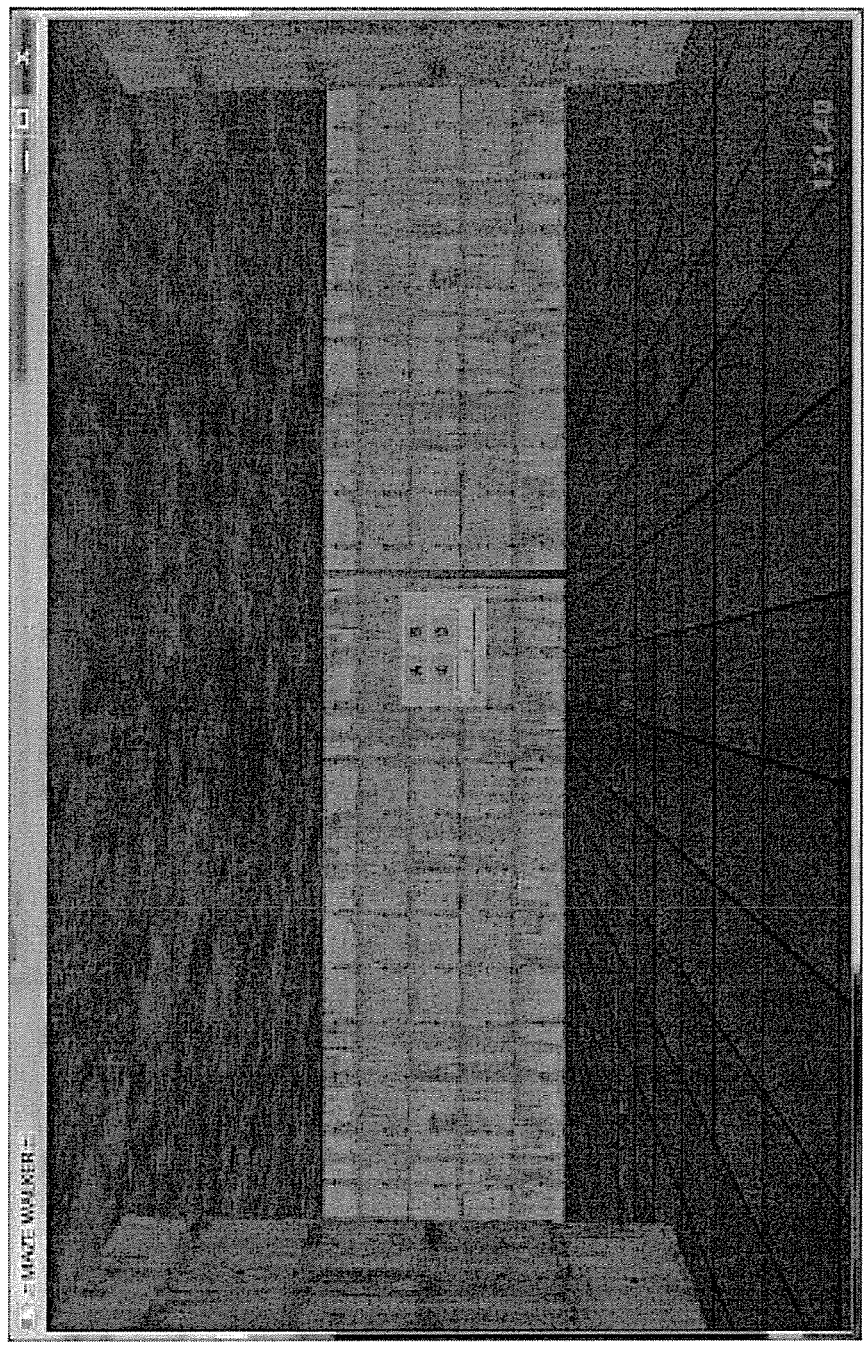
FIG. 11. depicts a capture image of the three dimensional environment.

Although not limited to the following, included herein is a description of fNIR in brain control interfaces, which, in one embodiment may be used in a three dimensional gaming environment. FIG. 10 depicts an example maze in a top down view as described below and FIG. 11 is a capture image of the three dimensional environment.

Using brain computer interface (BCI) devices, users can interact with computers in new ways other than the current computer control mechanisms (gaming controller, keyboard, mouse and joystick). However, BCI also presents inherent challenges so that a new paradigm and unique protocols are required by specific BCI systems due to the uncertainty in the functioning of both the brain activity monitoring devices and performing mental tasks by the subject along with the latency of brain signals that are measured. One approach is to integrate BCI in video games and integrate the challenges of using BCI within the gameplay. In traditional video games, the challenge to the user is simply the designed game mechanics. BCI based gameplay does not only involve the game mechanics based challenges, but also mastering the use of the BCI device itself. BCI may be added to current gaming platforms as a new or additional means of control for controlling, as one example, an avatar in a video game.

In one embodiment, a protocol was developed where users would need to engage with the bar task to accomplish their ultimate goal within task and as such fNIR-BCI would subserve their ultimate goal. To address this purpose, the game included spatial navigation task that would require participants to navigate within a 3D virtual environment with traditional keyboard buttons and their ultimate aim would be to reach exit locations. However, the gamer would need to engage with fNIR-BCI to interact with certain objects within this virtual environment. Since the ultimate aim was to navigate to exit locations, we selected doors as interactive objects that need to be opened only by fNIR-BCI and to be able to proceed, participants needed to successfully activate the fNIR-BCI. Although doors were selected, any other interactive object could have been selected. Integrating a Task protocol for control of interactive objects within this virtual environment where they have an ultimate aim of navigating to exit location and use the fNIR BCI to accomplish sub-goals and proceed that serves their ultimate aim.

During the experiment, fNIR sensor pad was positioned over the forehead of the participants while they were sitting in front of a computer screen and keyboard. Every 500 ms, raw fNIR signals of 16 voxels (2 wavelength and 1 dark current=48 channels) were sampled by COBI Studio at the data acquisition computer and sent through wired network to the Protocol Computer.

The fNIR-BCI Server software on the Protocol-Computer received the raw fNIR signals, calculated the oxygenation changes at real-time using modified Beer Lambert Law and transformed oxygenation changes to a number between 0 to 100, called fNIR-BCI index as described above. fNIR-BCI index is transmitted to the game at real-time through TCP/IP networking. The visual feedback (bar) for the fNIR-BCI was only visible when user approaches and stays in close proximity to interactive object (door). The visual feedback appeared vertical on the right hand side of the screen with a height close to screen height similar to bar-size control task. Critical event times such as activation of interactive objects were transmitted back to software through TCP/IP protocol for calculation of rest and task periods for online processing of fNIR signals.

The bar-size-control task was integrated within software for control of interactive objects in a 3D virtual environment. Within this maze task, doors were interactive objects. By increasing the fNIR-BCI index above a threshold, the action associated with the interactive object (i.e. opening door) was triggered. A virtual maze environment, called Arena, was designed to have 5 doors. First door is the entrance door and others are labeled A through D. Start position is just in front of the entrance door and exit (end regions) are behind each A, B, C and D doors. To navigate the 3D environment from beginning to end, users need to open two doors.

Learned self-regulation of cerebral dynamics can be utilized for a range of applications. One of the potential future directions for this fNIR BCI is to investigate the effect of fNIR neurofeedback training on cognitive abilities (i.e., learning/adaptation assessments as a function of the type and amount of practice along with feedback frequency and type of feedback). There is growing evidence in the literature that neurofeedback training has a positive effect on cognitive abilities. This fNIR-BCI could be helpful for use with older adults or in clinical populations where the decline in cognitive abilities can be curtailed with such training.

Moreover, fNIR-neurofeedback can be used in clinical populations for therapeutic applications of various psychiatric conditions. It has been shown that neurofeedback training can help regulate emotion networks in the brain and help improve perceived pain. Moreover, fNIR-neurofeedback may help stroke or Traumatic Brain Injury patients to exercise select brain regions for stimulating growth, neural and cognitive plasticity.

In another embodiment, a fNIR device may be integrated with an electroencephalography (EEG) system to provide control within a BCI computer environment or over a device. EEG is a technique that measures voltage fluctuations resulting from ionic current flows within the neurons of the brain during neural activity. An EEG system may comprise a device designed to measure and record these voltage fluctuations and allows time resolution at the level of one millisecond or faster, although spatial resolution may be poor. In this embodiment, signal from both an EEG system and an fNIR system may be integrated to provide greater precision in control of the BCI device.

In another embodiment, a fNIR device may be integrated with an electrooculagraph (EOG) and/or an eye tracker device to provide control within a BCI computer environment or over a device. EOG is a technique for measuring the resting potential of the retina, which allows the measurement of eye movements. In this embodiment, a signal from an EOG system may be integrated with an fNIR system to provide greater precision in control of the BCI device. The EOG system would allow tracking of eye-movements, for example, on a computer screen, with additional control (e.g., a selection device such as a "mouse-click") being provided through the signal from the fNIR device.

Finally, a simplified sensor and hardware system can be developed to have very low-cost, be very portable and wireless for deployment in the multimedia/gaming industry. We have already demonstrated that this paradigm can be deployed in gaming settings with new control mechanisms. Such a system can be used for entertainment applications for healthy populations and it can also be used for therapeutic applications (such as ADHD, PSTD, depression, anxiety and autism spectrum disorders).

What is claimed:

1. A system, comprising:
   one or more near infrared sources configured to emit infrared radiation onto a portion of a cortical region of a person;
   one or more detectors configured to receive infrared radiation indicative of a level of oxygenated hemoglobin and a level of deoxygenated hemoglobin in the portion of the cortical region;
   the system further comprising a feedback source configured to provide feedback to the person based on one or more of the level of oxygenated hemoglobin and the level of deoxygenated hemoglobin in the cortical region; and
   the system comprising a processor configured to correlate a change in the one or more of the level of oxygenated hemoglobin and the level of deoxygenated hemoglobin with a change in the feedback, the feedback being changed when a change in the one or more of the level of oxygenated hemoglobin and the level of deoxygenated hemoglobin is above a threshold value.

2. The system of claim 1, wherein the feedback is visual feedback.

3. The system of claim 1, wherein the feedback is a real time representation of deoxygenated hemoglobin in the cortical region.

4. The system of claim 1, wherein the feedback source comprises a display configured to provide a prompt to the person for initiating an up-regulation or down-regulation of deoxygenated hemoglobin in the cortical region.

5. The system of claim 1, wherein the processor is configured to determine that the one or more of the level of deoxygenated hemoglobin and the level of oxygenated hemoglobin in the cortical region indicates a level of concentration by the person.

6. The system of claim 1 wherein the processor is configured to determine that a change in one or more of the level of oxygenated hemoglobin and the level of deoxygenated hemoglobin indicates the person's intent to alter the feedback.

7. The system of claim 1, wherein the processor is configured to correlate the one or more of the level of oxygenated hemoglobin and the level of deoxygenated hemoglobin with the person's control of a binary, step, or continuous computing function.

8. The system of claim 7, the processor being further configured to correlate the one or more of the level of oxygenated hemoglobin and deoxygenated hemoglobin with the person's control of a binary or step computing function.

9. The system of claim 1, wherein the cortical region comprises the prefrontal cortex.

10. The system of claim 1, wherein the change in the feedback is based on a conversion parameter that controls a sensitivity in feedback to the change in oxygenated or deoxygenated hemoglobin levels.

11. A system, comprising:
one or more near infrared sources configured to emit infrared radiation onto a portion of a cortex of a person;
one or more detectors configured to receive infrared radiation indicative of a level of oxygenated hemoglobin and a level of deoxygenated hemoglobin of the portion of the cortex; and
the system comprising a feedback source configured to provide feedback to the person based on one or more of the level of oxygenated hemoglobin and the level of deoxygenated hemoglobin in the portion of the cortex; and
the system comprising a processor configured to correlate the one or more of the level of oxygenated hemoglobin and the level of deoxygenated hemoglobin in the portion of the cortex with a computing function, the feedback being changed when a change in the one or more of the level of oxygenated hemoglobin and the level of deoxygenated hemoglobin is above a threshold value.

12. The system of claim 11, wherein the feedback is visual feedback.

13. The system of claim 11, wherein the feedback is a real time representation of deoxygenated hemoglobin the in the portion of the cortex.

14. The system of claim 11, wherein the display is further configured to provide a prompt to the person for initiating an up-regulation or down-regulation of deoxygenated hemoglobin in the portion of the cortex.

15. The system of claim 11, wherein the processor is configured to correlate one or more of the level of oxygenated hemoglobin and the level of deoxygenated hemoglobin in the portion of the cortex to a level of concentration by the person.

16. The system of claim 11, wherein the portion of the cortex is a portion of the prefrontal cortex.

17. The system of claim 11, wherein the computing function is a binary or step computing function.

18. The system of claim 11, wherein the computer function is a continuous computing function.

19. The system of claim 11, wherein the first portion of the cortex comprises the prefrontal cortex.

20. The system of claim 11, wherein a change in the feedback is based on a conversion parameter that controls a sensitivity in the feedback to the change in oxygenated or deoxygenated hemoglobin levels.

21. A method for training a person to control a computer with a first portion of their cortical region, the method comprising:
emitting near infrared radiation from one or more emitters onto a portion of the cortical region;
receiving at a detector, first radiation from the portion of the cortical region, said first radiation including information indicative of one or more of a first level of oxygenated hemoglobin and a first level of deoxygenated hemoglobin of the portion of the cortical region;
providing to the person first feedback based on the one or more of the first level of oxygenated hemoglobin and the first level of deoxygenated hemoglobin of the portion of the cortical region;
receiving at a detector, second radiation from the portion of the cortical region, said second radiation including information indicative of one or more of a second level of oxygenated hemoglobin and a second level of deoxygenated hemoglobin of the portion of the cortical region; and
providing to the person second feedback based on the one or more of the second level of oxygenated hemoglobin and the second level of deoxygenated hemoglobin of the portion of the cortical region,
the second feedback being provided when a change between the one or more of the first and second levels of oxygenated hemoglobin and the first and second levels of deoxygenated hemoglobin is above a threshold value.

22. The method of claim 21, wherein first feedback and the second feedback are visual feedback.

23. The method of claim 22, further comprising iteratively adjusting at least one of the first and second feedback based on a change between the one or more of the first and second levels of oxygenated hemoglobin and the first and second levels of deoxygenated hemoglobin.

24. The method of claim 21, wherein providing to the person first feedback further comprises simultaneously determining a brain interface index of oxygenation levels, said brain interface index of oxygenation levels configured to provide a reference.

25. The method of claim 24, wherein the brain interface index comprises a predetermined dynamically adjusted scaling constant.

26. The method of claim 21, further comprising providing the person with binary or step control over a computing function, the binary or step control being based one or more of a level of oxygenated hemoglobin and a level of deoxygenated hemoglobin in the portion of the cortical region.

27. The method of claim 21, further comprising providing the person with continuous control over a computing function, the continuous control being based on one or more of a level of oxygenated hemoglobin and a level of deoxygenated hemoglobin in the portion of the cortical region.

28. The method of claim 21, wherein the portion of the cortical region comprises the prefrontal cortex.

29. The method of claim 21, wherein the second feedback is proportional to the change in oxygenated or deoxygenated hemoglobin levels.

30. The method of claim 29, wherein the second feedback is based on a conversion parameter that controls a sensitivity in the feedback to the change in oxygenated or deoxygenated hemoglobin levels.

31. The method of claim 30, further comprising changing the conversion parameter after providing the first or second feedback, changing the conversion parameter based on a characteristic of the person, or any combination thereof.

32. A method for determining the activation level of a portion of the cortex of a person, the method comprising:

emitting at least two wavelengths of near infrared radiation from one or more emitters onto the portion of the cortex;

receiving at a detector, radiation from the portion of the cortex, said radiation including information indicative of a level of oxygenated hemoglobin and indicative of a level of deoxygenated hemoglobin of the portion of the cortex;

determining the levels of oxygenated hemoglobin and deoxygenated hemoglobin, wherein the level of deoxygenated hemoglobin is determined independently from the level of oxygenated hemoglobin;

correlating one or both of the levels of oxygenated hemoglobin and deoxygenated hemoglobin to an activation level of the cortex; and providing a feedback to the person based on the activation level of the cortex.

33. The method of claim 32, wherein the portion of the cortex comprises the prefrontal cortex.

* * * * *